(12) United States Patent
Ashida et al.

(10) Patent No.: US 9,565,840 B2
(45) Date of Patent: Feb. 14, 2017

(54) FIBROTIC NON-HUMAN ANIMAL, AND USE THEREOF

(71) Applicants: KYOTO UNIVERSITY, Kyoto (JP); THE REGENTS OF THE UNIVERSITY OF CALIFORNIA, Oakland, CA (US)

(72) Inventors: Noboru Ashida, Kyoto (JP); Masayuki Yokode, Kyoto (JP); Michael Karin, La Jolla, CA (US); Dat Nguyen Tien, Kyoto (JP)

(73) Assignees: KYOTO UNIVERSITY, Kyoto (JP); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/439,885

(22) PCT Filed: Oct. 31, 2013

(86) PCT No.: PCT/JP2013/079623
§ 371 (c)(1),
(2) Date: Apr. 30, 2015

(87) PCT Pub. No.: WO2014/069597
PCT Pub. Date: May 8, 2014

(65) Prior Publication Data
US 2015/0320020 A1 Nov. 12, 2015

Related U.S. Application Data

(60) Provisional application No. 61/721,301, filed on Nov. 1, 2012.

(51) Int. Cl.
*A01K 67/027* (2006.01)
*A61K 49/00* (2006.01)
*G01N 33/50* (2006.01)
*C12N 9/12* (2006.01)
*C12N 15/09* (2006.01)

(52) U.S. Cl.
CPC ......... *A01K 67/0276* (2013.01); *A01K 67/027* (2013.01); *A61K 49/0008* (2013.01); *C12N 9/12* (2013.01); *C12N 15/09* (2013.01); *G01N 33/5008* (2013.01); *A01K 2217/075* (2013.01); *A01K 2217/15* (2013.01); *A01K 2217/206* (2013.01); *A01K 2227/105* (2013.01); *A01K 2267/035* (2013.01); *A01K 2267/0387* (2013.01); *C12Y 207/1101* (2013.01)

(58) Field of Classification Search
CPC ............ A01K 2217/075; A01K 2217/15; A01K 2217/206; A01K 2227/105; A01K 2267/035; A01K 2267/0387; A01K 67/027; A01K 67/0276
USPC .............................................. 800/18, 9, 13
See application file for complete search history.

(56) References Cited

U.S. PATENT DOCUMENTS

2002/0156000 A1 10/2002 May et al.
2010/0261701 A1 10/2010 Kaneko et al.

FOREIGN PATENT DOCUMENTS

JP   2012-100663   5/2012
WO  2010/038465   4/2010

OTHER PUBLICATIONS

Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369.*
Prelle et al. (2002) Anat. Histol. Embryol., vol. 31, 169-186.*
Munoz et al. (2009) Stem Cell Rev. and Rep., vol. 5, 6-9.*
Mullins et al. (1996) J. Clin. Invest., vol. 98(11), S37-S40.*
Li et al. (2003). J. Immuno., vol. 170, 4630-4637.*
Roman-Blas et al. (2008) Scleraderma Center Faculty Papers, Paper 1, http://jdc.jefferson. edu/sclerodermafp/1.*
Elsharkawy et al. (2007) Hepatology vol. 46, 590-597.*
Ashida et al. (2011) Nature Communications, online, http://www.nature.com/ncomms/journal/v2/n5/full/ncomms1317.html, pp. 1-9.*
International Search Report dated Jan. 28, 2014, issued in International Patent Application No. PCT/JP2013/079623.
Ashida, Noboru, "Pleiotropic role of IKKβ", Journal of Clinical and Experimental Medicine, Jun. 23, 2012, vol. 241, No. 12, pp. 919-920.
Ashida et al., "IKKβ relgulates essential functions of the vascular endothelium through kinase-dependent and -independent pathways", Nature Communications [online], May 17, 2011, internet, URL:http:http//www.nature.com/ncomms/journal/v2/n5/full/ncomms1317.html.
Yamamoto et al., "Animal Model of Sclerotic Skin. I: Local Injections of Bleomycin Induce Sclerotic Skin Mimicking Scleroderma", The Society for Investigative Dermatology, Inc., vol. 112, No. 4, Apr. 1999, pp. 456-462.
Mori et al., "Role and Interaction of Connective Tissue Growth Factor with Transforming Growth Factorβ in Persistent Fibrosis: A Mouse Fibrosis Model", Journal of Cellular Physiology, vol. 181, 1999, pp. 153-159.
Green et al., "Tight-Skin, a New Mutation of the Mouse Causing Excessive Growth of Connective Tissue and Skeleton", American Journal of Pathology, vol. 82, No. 3, Mar. 1976, pp. 493-512.
Siracusa et al., "A Tandem Duplication within the fibrillin 1 Gene is Associated with the Mouse Tight skin Mutation", Genome Research, www.genome.cshlp.org, vol. 6, 1996, pp. 300-314.
Loeys et al., "Mutations in Fibrillin-1 Cause Congenital Scleroderma: Stiff Skin Syndrome", Sci. Transl. Med., vol. 2, No. 23, Mar. 17, 2010, pp. 1-25.
Shin Maeda, et al. "IKKβ Is Required for Prevention of Apoptosis Mediated by Cell-Bound but Not by Circulating TNFα", Immunity, 2003, vol. 19, pp. 725-737.

(Continued)

Primary Examiner — Anne Marie S Wehbe
(74) Attorney, Agent, or Firm — Wenderoth, Lind & Ponack, L.L.P.

(57) ABSTRACT

The present invention provides a non-human animal IKKβ which shows fibrosis of tissue, since it lacks IKKβ gene in a myofibroblast- and/or smooth muscle cell-specific manner. Since the non-human animal shows pathology highly similar to scleroderma, it is extremely useful as an animal model of scleroderma.

14 Claims, 22 Drawing Sheets

(56) References Cited

OTHER PUBLICATIONS

Tom Luedde, et al., "Deletion of IKK2 in hepatocytes does not sensitize these cells to TNF-induced apoptosis but protects from ischemia/reperfusion injury", The Journal of Clinical Investigation, 2005, vol. 115, No. 4, pp. 849-859.

Jeongeun Hyun, et al., "Potential role of Hedgehog signaling and microRNA-29 in liver fibrosis of IKKβ-deficient mouse", J. Mol. Hist., 2014, vol. 45, pp. 103-112.

Tadashi Yoshida, et al., "Smooth Muscle-Selective Inhibition of Nuclear Factor-κB Attenuates Smooth Muscle Phenotypic Switching and Neointima Formation Following Vascular Injury", Journal of the American Heart Association, 2013; 2:e000230 doi;10.1161/JAHA. 113.000230, pp. 1-14.

Extended European Search Report completed May 27, 2016, and mailed Jun. 10, 2016, issued in corresponding European Patent Application No. 13851788.3.

Youngmi Jung et al., "Signals from Dying Hepatocytes Trigger Growth of Liver Progenitors", Gut, 2010, vol. 59, No. 5, pp. 655-665.

Philippe Boucher et al., "LRP: Role in Vascular Wall Integrity and Protection from Atherosclerosis", Science, 2003, vol. 300, No. 5617, pp. 329-332.

Alexandra Balbir-Gurman et al., "Scleroderma—New aspects in pathogenesis and treatment", Best Practice & Research Clinical Rheumatology, 2012, vol. 26, No. 1, pp. 13-24.

Jérôme Avouac et al., "Experimental models of dermal fibrosis and systemic sclerosis", Joint Bone Spine, 2013, vol. 80, No. 1, pp. 23-28.

Toshiyuki Yamamoto, "Animal model of systemic sclerosis", Journal of Dermatology, 2010, vol. 37, No. 1, pp. 26-41.

Andrea Oeckinghaus et al., "Crosstalk in NF-κB signaling pathways", Nature Immunology, vol. 12, No. 8, 2011, pp. 695-708.

Alain Chariot, "The NF-κB-independent functions of IKK subunits in immunity and cancer", Trends Cell Biol., vol. 19, No. 8, 2009, pp. 404-413.

\* cited by examiner

Fig. 9-1
(a)
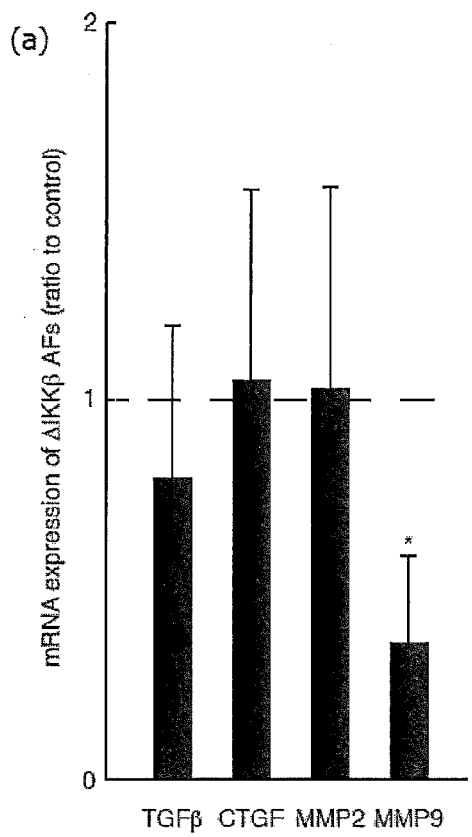
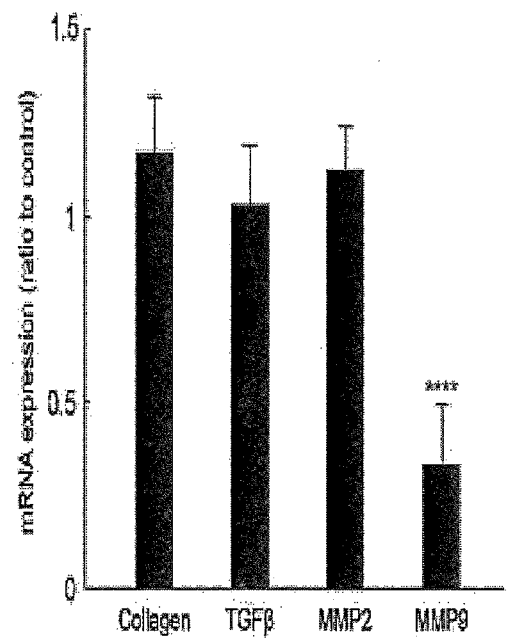
(b)
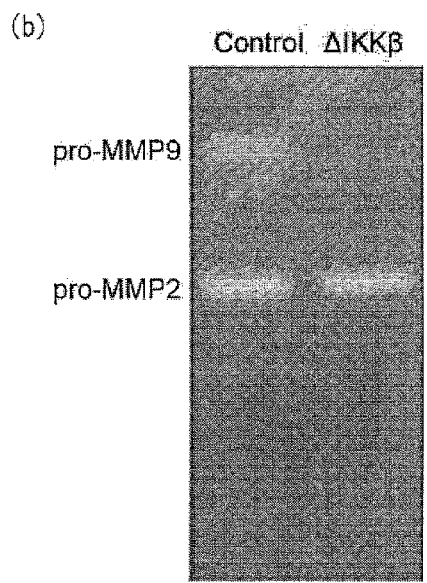
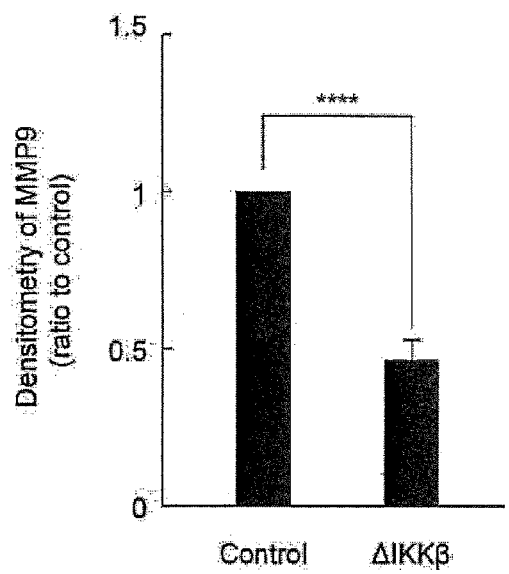

us 9,565,840 B2

SEQUENCE LISTING

```
<160> NUMBER OF SEQ ID NOS: 2

<210> SEQ ID NO 1
<211> LENGTH: 34
<212> TYPE: DNA
<213> ORGANISM: Artificial Sequence
<220> FEATURE:
<223> OTHER INFORMATION: Synthetic loxP sequence

<400> SEQUENCE: 1
ataacttcgt atagcataca ttatacgaag ttat                               34

<210> SEQ ID NO 2
<211> LENGTH: 34
<212> TYPE: DNA
<213> ORGANISM: Artificial Sequence
<220> FEATURE:
<223> OTHER INFORMATION: Synthetic frt sequence

<400> SEQUENCE: 2
gaagttccta ttctctagaa agtataggaa cttc                               34
```

FIBROTIC NON-HUMAN ANIMAL, AND USE THEREOF

This invention was made with government support under AI043477 awarded by National Institutes of Health. The government has certain rights in the invention.

TECHNICAL FIELD

The present invention relates to a fibrotic non-human animal and use thereof. More particularly, the present invention relates to a non-human animal that characteristically shows fibrosis of tissue by deleting IKKβ gene in a myofibroblast- and/or smooth muscle cell-specific manner, and a method of screening for a prophylactic and/or therapeutic drug for fibrosis by using the non-human animal and the like.

BACKGROUND ART

Fibrosis of tissue accompanying deposition of collagenous fiber is a phenomenon that occurs during wound healing process in the body as a terminal state of an inflammation reaction, and plays an important role in wound healing and the like in the body. On the other hand, excessive fibrosis of tissue is considered an onset or aggravating factor of various diseases based on inflammation, for example, dermatic disease, cardiac disease, respiratory disease, autoimmune disease, collagen disease, cancer, arteriosclerosis, diabetes and the like. Moreover, the mechanism of fibrosis has not been sufficiently elucidated, and the treatment of these diseases accompanying fibrosis is difficult.

Scleroderma (systemic scleroderma) which is one of the collagen diseases, is a disease mainly comprising enhanced synthesis and accumulation of collagenous fiber in the skin and internal organs. The disease characteristically shows a male-to-female ratio of about 1:9, and occurs in many females in the middle age of 30-50 years old. The pathology thereof also includes skin lesions such as Raynaud's symptoms, skin hardening and the like, as well as internal organ diseases such as lung fibrosis, renopathy, reflux oesophagitis and the like. Therefore, scleroderma is an intractable disease that affects not only the quality of life but also life prognosis, and at present, an effective treatment method and the like have not been established.

Conventionally, an animal model used for fibrosis, particularly, scleroderma, is a mouse having an artificially-developed fibrosis by the administration of drugs such as bleomycin and the like, cytokines such as TGFβ (transforming growth factor beta), CTGF (connective tissue growth factor), bFGF (basic fibroblast growth factor) and the like (non-patent documents 1, 2), or Tight skin mouse having gene abnormality at Fibrillin-1 (non-patent documents 3, 4). However, these known animal models have problems since, when, for example, a mouse is administered with cytokine in the skin, the skin of the administration site is only topically hardened, Tight skin mouse shows skin hardening of the equivalent level for male and female, and renopathy, reflux oesophagitis and the like are not observed, and the like. Therefore, all known animal scleroderma models are not sufficient in terms of the similarity to the pathology in human, artificiality and the like. Moreover, since Fibrillin-1 was reported to be a responsible gene of Stiff Skin Syndrome, which is a genetic disease completely different from scleroderma (non-patent document 5) in recent years, usefulness of tight skin mouse as a scleroderma model mouse has been questioned.

DOCUMENT LIST

Non-Patent Documents non-patent document 1: Yamamoto T. et al., Animal model of sclerotic skin. I: Local injections of bleomycin induce sclerotic skin mimicking scleroderma, (1999), J. Invest. Dermatol., vol. 112, no. 4, p. 456-462 non-patent document 2: Mori T. et al., Role and interaction of connective tissue growth factor with transforming growth factor-β in persistent fibrosis: A mouse fibrosis model, (1999), J. Cell Physiol., vol. 181, no. 1, p. 153-159 non-patent document 3: Green M. C. et al., Tight-skin, a new mutation of the mouse causing excessive growth of connective tissue and skeleton, (1976), Am. J. Pathol., vol. 82, no. 3, p. 493-512 non-patent document 4: Siracusa L. D. et al., A tandem duplication within the fibrillin 1 gene is associated with the mouse tight skin mutation, (1996), Genome Res., vol. 6, no. 4, p. 300-313 non-patent document 5: Loeys B. L. et al., Mutations in fibrillin-1 cause congenital scleroderma: stiff skin syndrome, (2010), Sci. Transl. Med., vol. 2, no. 23, p. 23ra20.

SUMMARY OF THE INVENTION

Problems to be Solved by the Invention

The present invention provides a highly useful non-human fibrotic animal showing fibrosis of tissue, which is observed in various diseases, and use thereof. Moreover, the present invention provides an animal model of scleroderma from among fibrotic animal models. Furthermore, in the present invention, the animal model is used to elucidate fibrosis of tissue or the mechanism of scleroderma. The present invention also provides a method of screening for a substance for the prophylaxis or, treatment of fibrosis of tissue or scleroderma, by using the animal model. In addition, the present invention utilizes production of an autoantibody by the animal model and applies same to the elucidation of the production mechanism of autoantibody.

Means of Solving the Problems

The present inventors have observed skin hardening with erosion in head, tail of mouse engineered to delete IKKβ gene in a myofibroblast- and/or smooth muscle cell-specific manner (hereinafter to be also referred to as "knockout mouse", "KO mouse", "ΔIKKβ" or "IKKβ$^{\Delta MF}$") and surprisingly found histologically marked thickening of epidermis and dermis and marked accumulation of collagenous fiber (hereinafter to be also referred to as "collagen"). Furthermore, they have found that the mouse shows substitution of collagenous fiber for smooth muscle below mucosa in the lower oesophagus and expansion of oesophagus; accumulation of collagenous fiber and alveolar enlargement, and enlargement of right ventricle suggesting lung hypertension in the lung; accumulation of collagenous fiber and stenosis of afferent and efferent glomerular arteries in the kidney, and increase in urinary protein, hypertension and the like seemingly caused thereby. That is, the mouse showed fibrosis in various tissues or organs such as skin, oesophagus, lung, kidney and the like, and also shows various symptoms associated therewith such as enlargement of right ventricle, hypertension and the like.

Furthermore, they have found that the ratio of male and female that developed erosive skin lesion is biased and 3 to 4 times higher in female mice than in male mice. Surprisingly, moreover, since mouse showing the aforementioned lesion also produces autoantibody detected specifically in patients, like the scleroderma patients, and also shows enlargement of spleen, the mouse was concluded to strongly reflect the pathology of human scleroderma. Finally, they have found that the mice suddenly die after one year and that cancer is observed in the kidney of the dead mice.

In addition, the present inventors have also found that, when fibroblast and dendritic cell prepared from the mouse are co-cultivated, stimulation of T cell by antigen presentation increases.

The present inventors have also found that nuclear and total cellular expression levels of NFκB p65 decrease and the NFκB activity decreases in the fibroblasts prepared from the skin of scleroderma patients. They have also clarified the possibility that the decrease in the NFκB activity is the basic mechanism of the onset of the scleroderma pathology.

The present inventors conducted intensive studies based on these findings and completed the present invention. That is, the present invention is as follows:

[1] A non-human animal showing fibrosis of tissue, which lacks IKKβ gene in a myofibroblast- and/or smooth muscle cell-specific manner, or a part of the living body thereof.
[2] The non-human animal or a part of the living body thereof of [1], wherein the fibrosis of tissue reproduces fibrosis associated with a disease selected from the group consisting of autoimmune disease, collagen disease, dermatic disease, cardiac disease, respiratory disease, oesophagus disease, stomach gastrointestinal disease, hepatic disease, renal disease, cranial nerve disease, cancer and diabetes.
[3] The non-human animal or a part of the living body thereof of [1], which is a scleroderma model.
[4] The non-human animal or a part of the living body thereof of [1], wherein the animal is rodent.
[5] A method of screening for a substance for the prophylaxis and/or treatment of fibrosis of tissue, comprising
(a) a step of contacting a test substance with the non-human animal or a part of the living body thereof of [1], and
(b) a step of analyzing fibrosis of a tissue of the aforementioned non-human animal or a part of the living body thereof of [1].
[6] A method of screening for a substance for the prophylaxis and/or treatment of scleroderma, comprising
(a) a step of contacting a test substance with the non-human animal or a part of the living body thereof of [1], and
(b) a step of analyzing an event reflecting pathology scleroderma of the aforementioned non-human animal or a part of the living body thereof of [1].

Effect of the Invention

The present invention can provide a more practical fibrotic animal model. Since the animal model shows fibrosis in various tissues or organs, it can be used for elucidating a conventionally unknown mechanism of fibrosis. Also, the present invention is useful since it can provide a screening method of a substance for the prophylaxis or treatment of fibrosis by using the fibrotic animal model.

Moreover, the present invention can provide an animal scleroderma model showing pathology more similar to the pathology of human, as compared to conventional fibrotic, particularly scleroderma, animal models. The animal model can be used for elucidating a conventionally unknown mechanism of scleroderma. The present invention is also useful since it can provide a screening method of a substance for the prophylaxis or treatment of scleroderma by using the fibrotic animal model.

In addition, since the non-human animal of the present invention produces an autoantibody similar to that of scleroderma patients, and T cells are activated by co-cultivating fibroblast derived from the animal and antigen presenting cells, the non-human animal of the present invention can be applied to the elucidation of abnormal enhancement of immune reaction and production mechanism of autoantibody and is extremely useful.

BRIEF DESCRIPTION OF THE DRAWINGS

FIG. 1-2 shows microscopic images of the results of immunostaining of each of hair follicle (left) and artery (right) of knockout mouse, and shows lack of IKKβ in smooth muscle cell or myofibroblast (SM22α$^+$).

FIG. 2(a) shows photographs of 4 weeks old, and 16 weeks old knockout mouse (ΔIKKβ). The knockout mouse shows skin hardening with erosion. FIG. 2(b) shows the analysis results of the skin tissues of knockout mouse and wild-type mouse. Knockout mouse showed thickening of epidermis and dermis and marked accumulation of collagenous fiber. In contrast, the wild-type mouse did not show the aforementioned lesion.

FIG. 4-1 shows microscopic images (left) showing the results of Masson's trichrome staining of the oesophagus of knockout mouse (ΔIKKβ) and wild-type mouse (control) (lower panels are magnified images of the parts in square in the upper panels), and the length of the oesophageal muscularis mucosa of the both mice (right). Knockout mouse shows substitution of collagenous fiber for smooth muscle below mucosa in the lower oesophagus and expansion of oesophagus.

FIG. 4-2 shows microscopic images (upper) showing the results of Masson's trichrome staining of the lung of knockout mouse (ΔIKKβ) and wild-type mouse (control), and the size of the alveolus of the both mice (lower). Knockout mouse shows accumulation of collagenous fiber and enlargement of alveolus in the lung.

FIG. 4-3 shows photographs (upper) of the hypertrophic right ventricle of knockout mouse (ΔIKKβ) and wild-type mouse (control) and the area (lower) of the right ventricle of the both mice. Knockout mouse showed enlargement of the right ventricle suggesting lung hypertension.

FIG. 4-4 shows a microscopic image (left) of the results of picrosirius red/fast green staining of the renal glomerulus of knockout mouse (ΔIKKβ), as well as comparison with wild-type mouse (control) of urine protein/creatinine ratio (middle) and blood pressure (right). Accumulation of collagenous fiber in the kidney and an increase in urine protein and hypertension are observed.

FIG. 6-1 shows microscopic images of the liver after DAB staining which show the presence or absence of an autoantibody in the sera derived from knockout mouse (ΔIKKβ) and wild-type mouse (control), and the proportion (%) of stained area. Knockout mouse shows the presence of autoantibody.

FIG. 6-2 shows photographs of the spleen of knockout mouse (ΔIKKβ) and wild-type mouse (control), and the weight of the spleen of the both mice. Knockout mouse showed enlargement of the spleen.

FIG. 6-3 shows photographs of the spleen of the knockout mouse (IKKβ$^{\Delta MF}$) and wild-type mouse (control) stained with peanuts agglutinin (PNA), which is a marker of activated B cells and germinal center. Knockout mouse showed activation of B cells.

FIGS. 9-1 and 9-2 show that IKKβ controls the expression or activity of matrix metalloproteinase9 (MMP9). Fibroblasts were prepared from the skin tissue of knockout mouse (ΔIKKβ), mRNA and protein were extracted, and the expression level of mRNAs of various regulatory factors of collagen was verified by qRT-PCR method (FIG. 9-1($a$)), and the activity of MMP protein was verified by gelatin zymography method (FIG. 9-1($b$)). As a result, the knockout mouse showed a marked decrease in the mRNA expression and activity of MMP9 as compared to the control.

FIG. 9-2 shows that mRNA and the activity of MMP9 markedly increased when IKKβ was overexpressed (IKKβKA).

FIGS. 9-3 and 9-4 show that IKKβ regulates expression of β-catenin. FIG. 9-3 shows that the expression of active β-catenin increased in IKKβ knockout mouse (ΔIKKβ) and decreased in IKKβ overexpression mouse (IKKβKA).

FIG. 9-4 shows the results of detection of coprecipitated IKKβ-β-catenin by immunoblotting by using an anti-β-catenin antibody or an anti-FLAG antibody, after immunoprecipitation (IP) of fibroblast lysate (1 mg) of mouse that overexpresses IKKβ having a FLAG tag with 1 μg of control IgG, anti-FLAG antibody (upper) or anti-β-catenin antibody (lower).

FIGS. 11-1 to 11-3 show suppression of IKKβ and NFκB in the fibroblasts of scleroderma patients. The p65 protein amount in whole cell lysate (FIG. 11-1($a$)) and nuclear extract (FIG. 11-1($b$)) (Western blot images (left), results of densitometry (middle)), p65 gene expression level (FIG. 11-1($a$) right), and NFκB activity (FIG. 11-1($b$) right) in the fibroblasts derived from the skin of the scleroderma patients and healthy individual were examined. The fibroblast of scleroderma patients showed a decrease in the expression of p65 and NFκB activity.

FIG. 11-2 shows changes in IKKβ and p65 proteins in whole cell lysate (left) and nuclear extract (right) of fibroblasts derived from the skin of scleroderma patients and healthy individual, when stimulated with IL-1β (2.5 ng/mL) for 60 min.

FIG. 11-3 shows changes in the IKKβ expression in fibroblast of scleroderma patients when treated with 2 μM MG132 for 2 hr before IL-1β stimulation.

DESCRIPTION OF EMBODIMENTS

Figure 1:
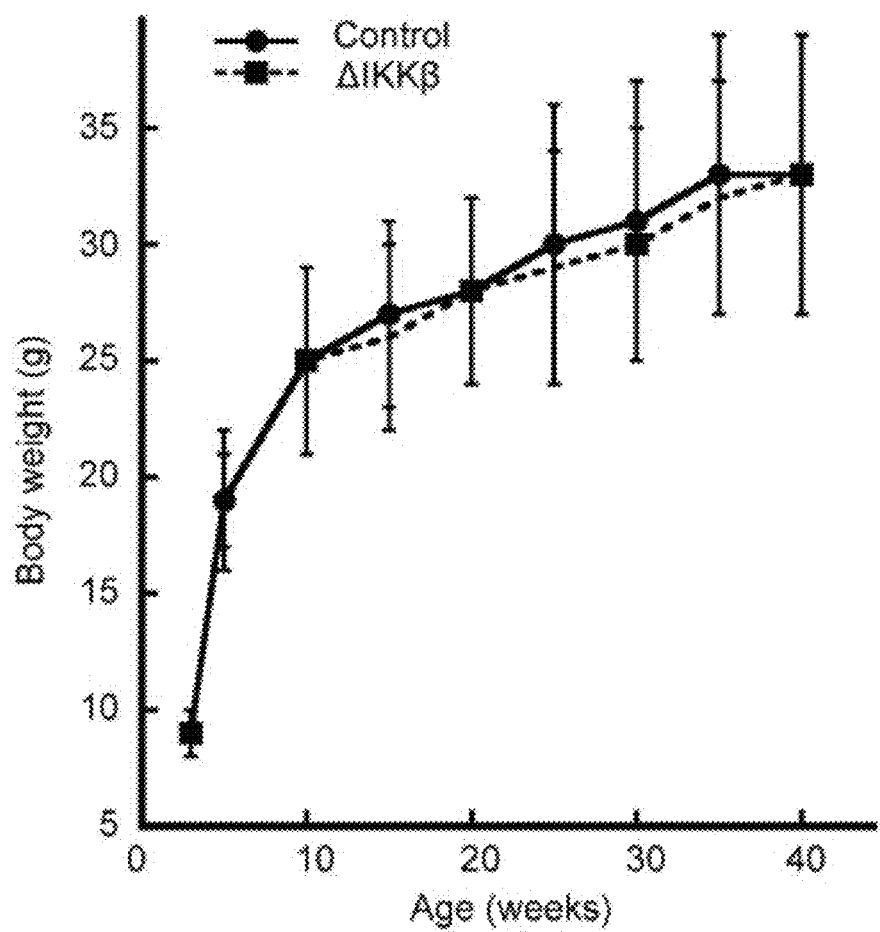
FIG. 1-1 shows changes in the body weight of knockout mouse (ΔIKKβ) and wild-type mouse (control).

The present invention is explained in detail below.

Fibrosis

Fibrosis of a tissue refers to a state where extracellular substrates such as fibronectin, collagenous fiber and the like are markedly deposited on the tissue, or a marked increase in collagenous fibers results in increased fibrotic connective tissues to leave scar tissues.

Examples of the disease showing tissue fibrosis include autoimmune disease, collagen disease, dermatic disease, cardiac disease, respiratory disease, oesophagus disease, gastrointestinal disease, hepatic disease, renal disease, cranial nerve disease, ophthalmic disease, bone marrow disease, cancer, arteriosclerosis, diabetes and the like, but are not limited to these diseases as long as tissue fibrosis is observed. Since the fibrotic animal model of the present invention well reproduces fibrosis associated with the above-mentioned various diseases, it can be useful for the study of fibrosis as an onset or aggravation factor of these diseases, development of a treatment means for the diseases using improvement of fibrosis as an index and the like.

More specifically, examples of the autoimmune disease include pemphigus, Graves' disease and the like. Examples of the collagen disease include scleroderma (systemic scleroderma including diffuse scleroderma or localized scleroderma, or localized scleroderma including linear scleroderma or scleroderma enplaques), rheumatoid arthritis, systemic lupus erythematosus, Sjogren's syndrome and the like. Examples of the dermatic disease include scleroderma (systemic scleroderma including diffuse scleroderma or localized scleroderma, or localized scleroderma including linear scleroderma or scleroderma enplaques) and the like. Examples of the cardiac disease include cardiomyopathy such as restrictive cardiomyopathy and the like, endomyocardial fibrosis, myocardial infarction, angina pectoris, cardiac failure, hypertensive cardiac disease and the like. Examples of the respiratory disease include lung fibrosis such as drug-induced lung fibrosis, idiopathic lung fibrosis or idiopathic interstitial pneumonia and the like, and the like. Examples of the oesophagus disease include reflux oesophagitis, muscle fiber hypertrophy congenital oesophageal stenosis and the like.

Examples of the gastrointestinal disease include ulcerative colitis, Crohn's disease, cystic fibrosis, pancreatitis and the like. Examples of the hepatic disease include hepatitis, cirrhosis and the like. Examples of the renal disease include nephritis, nephrosclerosis, chronic kidney disease, diabetic nephropathy, scleroderma renal crisis, renal failure and the like. Examples of the cranial nerve disease include Alzheimer's disease, progressive supranuclea palsy, corticobasal degeneration, familial frontotemporal dementia, neurofibromatosis and the like. Examples of the ophthalmic disease include thyroid eye disease, Graves' disease and the like. Examples of the bone marrow disease include bone marrow fibrosis and the like. Cancer includes cancer of various tissues or organs, for example, brain, tongue, pharyngis, skin, oesophagus, lung, mamma, stomach, pancreas, liver, gall bladder, bile duct, small intestine, large intestine, kidney, bladder, prostate, uterus, ovary, blood vessel, bone marrow and the like. Arteriosclerosis includes non-atherosclerotic disease, arteriosclerosis and the like. Diabetes includes type 1 diabetes, type 2 diabetes, secondary diabetes, diabetes due to abnormality of particular gene and the like.

Being "myofibroblast- and/or smooth muscle cell-specific" means being specific only to "myofibroblast", or only to "smooth muscle cell" or specific to both cells of "myofibroblast and smooth muscle cell". Preferred is being specific to myofibroblast alone or specific to both myofibroblast and smooth muscle cell.

That "lacks IKKβ gene" in a myofibroblast- and/or smooth muscle cell-specific manner refers to a state where normal function that IKKβ gene intrinsically has cannot be exhibited sufficiently, for example, a state where IKKβ gene is not expressed at all, a state where the expression level of IKKβ gene is low to the extent that the normal function it intrinsically has cannot be exhibited, a state where the function of IKKβ gene product is completely lost, or a state where the function of IKKβ gene product is lowered to the extent that the normal function IKKβ gene intrinsically has cannot be exhibited due to gene mutation and the like.

In the present invention, fibrosis of tissue and the like can be confirmed by a method known per se such as visual observation, histological analysis, image analysis (ultrasonic waves, CT, MR etc.), blood biochemical analysis and the like.

Examples of the immunological method known per se include immunohistochemical staining method, Western blot method, enzyme immunoassay (EIA) (e.g., direct competitive ELISA, indirect competitive ELISA, sandwich ELISA), radioimmunoassay (RIA), fluorescence immunoassay (FIA) and the like. Various kits and the like utilizing these methods are also known, and those of ordinary skill in the art can appropriately use same according to the object. For example, MESACUP (registered trade mark) anti-RNA polymerase III test (MBL), MESACUP (registered trade mark)-2 test CENP-B (MEL), MESACUP (registered trade mark) ANA test (MBL), fluoro HEPANA test (MBL) and the like used for the diagnoses of scleroderma patients can be used.

Non-Human Animal

A non-human animal lacking IKKβ gene in a myofibroblast- and/or smooth muscle cell-specific manner can be obtained by (a) a step of preparing a non-human animal wherein a gene encoding a site-specific recombination enzyme contiguous to a marker gene expressed in a myofibroblast- and/or smooth muscle cell-specific manner is present in a gene locus, (b) a step of preparing a non-human animal having a recognition site of the aforementioned site-specific recombination enzyme in the IKKβ gene locus, and crossing the non-human animals of the aforementioned (a) and (b). As long as IKKβ is lacking in a myofibroblast- and/or smooth muscle cell-specific manner, the method is not limited to the above method.

As for IKKβ gene, sequences derived from various species are known and, for example, sequences such as mouse (GenBank Accession No. AF026524), rat (GenBank Accession No. NM_053355), chicken (GenBank Accession No. NM_001031397.1), chimpanzee (GenBank Accession No. XM_528121.2) and the like can be utilized. Furthermore, homologues thereof and the like can also be used.

Examples of the marker gene that expresses in a myofibroblast- and/or smooth muscle cell-specific manner include, but are not limited to, Sm22α (Smooth muscle 22α), αSMA (α smooth muscle actin), SMMHC (smooth muscle myosin heavy chain) and the like. Examples of the site-specific recombination enzyme contiguous to a marker gene include recombinase, more specifically Cre protein. As a recognition site when Cre protein is used, loxP sequence (5'-ATAACTTCGTATAGCATACATTATACGAAGTTAT-3'; SEQ ID NO: 1) can be mentioned, including the loxP sequences that undergo optional deletion, substitution, addition and the like as long as they can be recognized by Cre protein.

To obtain a non-human animal having a locus encoding a site-specific recombination enzyme contiguous to a marker gene expressed in a myofibroblast- and/or smooth muscle cell-specific manner is present in the gene locus, a vector wherein a gene encoding a Cre protein is linked to the downstream of a promoter of the marker is constructed. For example, when the marker gene is SM22α, a vector wherein a gene encoding a Cre protein is linked to the downstream of a promoter of SM22α gene is constructed. The non-human animal can be obtained by introducing the vector into a germ line of the non-human animal such as mouse, rat and the like. As the animal, for example, a transgenic mouse is known (e.g., SM22α-Cre mouse is commercially available from Jackson Laboratory (stock numbers 004746, 006878)). Alternatively, it can be produced by the method of Science (2003), vol. 300, p. 329-332.

A non-human animal having the loxP sequence in the IKKβ gene locus can be produced by a method known per se, for example, by reference to Rajewsky K et al., Conditional gene targeting., J. Clin. Invest., (1996), 98(3), p. 600-603 and the like. More specifically, a targeting vector wherein the loxP sequence and a drug-selection marker gene such as neomycin resistance (NeoR) gene are inserted into IKKβ gene (intron etc.) for sandwiching (lethal gene such as thymidine kinase (TK), diphtheria toxin and the like is desirably further inserted outside the IKKβ gene) is constructed, and the targeting vector is introduced into ES cell or iPS cell. For introduction, electroporation method, lipofection method, microinjection method, calcium phosphate method and the like can be performed. When Neo/TK is used as a selection marker, GT418 resistance and gancyclovir resistance colony is selected, whereby a clone wherein a cassette containing NeoR gene sandwiched between loxP sequences is inserted into the IKKβ gene locus by homologous recombination can be obtained. Then, chromosome DNA is extracted from a single colony, and a known means such as Southern hybridization method, PCR method and the like is used to verify that the object ES cell or iPS cell introduced with the targeting vector has been obtained. Furthermore, the ES or iPS cell is introduced into an embryo derived from a non-human animal to prepare a chimera embryo, the chimera embryo is implanted to the uterus or oviduct of an animal other than human to develop a chimeric animal. For example, a mouse having a gene locus wherein IKKβ gene sandwiched between loxP sequences (flox mouse) is known (e.g., J. Immunol., (2003), vol. 170, p. 4630-4637).

Besides the above-mentioned, a Cre-loxP system and an FLP-frt system may be combined to remove influence of a drug selection marker on the aforementioned targeting vector, by sandwiching the drug selection marker with frt sequences (5'-GAAGTTCCTATTCTCTAGAAAGTATAG-GAACTTC-3'; SEQ ID NO: 2) and allowing FLP to act in a suitable stage to remove the drug selection marker. The aforementioned frt sequence includes a ftr sequence that undergoes optional deletion, substitution, addition and the like as long as it can be recognized by the FLP protein.

An animal to be introduced with the aforementioned targeting vector may be any as long as it is other than human, and includes a transgenic animal and animals for which a production method of ES cell and/or iPS cell has been established. For example, rodents such as mouse, rat, hamster, guinea pig and the like, rabbit, swine, bovine, chicken, goat, horse, sheep, dog, cat, monkey and the like can be mentioned. Preferably, rodents, more preferably mouse, rat, hamster and guinea pig can be mentioned.

Since the non-human animal of the present invention obtained by the aforementioned method, which lacks IKKβ gene in a myofibroblast- and/or smooth muscle cell-specific manner, for example, the mouse described in the below-mentioned Examples, which lacks IKKβ gene in a myofibroblast- and/or smooth muscle cell-specific manner, shows fibrosis of various tissues or organs, it can be used as an animal model of fibrosis. More specifically, the non-human animal of the present invention shows phenotype of fibrosis of at least the skin and other tissue or organ, for example, oesophagus, lung, kidney and the like. Furthermore, in one embodiment, the skin of the non-human animal (e.g., mouse) shows an increase in the expression of collagen I, TGFβ and β-catenin. In another embodiment, the non-human animal shows thickening of epidermis and dermis not only in the lesion part but also in non-lesion parts (apparently normal skin). In still another embodiment, the non-human animal did not show enhancement of collagen deposition in vascular smooth muscle cells in aorta and the like, irrespective of lacking or not lacking IKKβ in smooth muscle cells. Also, the non-human animal of the present invention markedly develops pathology of fibrosis in female compared to male.

Moreover, the non-human animal of the present invention shows not only fibrosis of various tissues but also enlargement of right ventricle, hypertension, enlargement of spleen and the like; produces autoantibody (anti-centromere antibody etc.) detected specifically in scleroderma patients; and shows activation of B cells and T cells in the spleen. That is, since the non-human animal strongly reflects the pathology of scleroderma, it can also be used as an animal model of scleroderma.

The present invention also provides a part of the living body of a non-human animal obtained by the aforementioned method and use thereof. For example, it is possible to collect blood from the non-human animal, and use the blood or a product prepared therefrom. Alternatively, it is also possible to partly collect various tissues or organs of the non-human animal, and use a prepared product such as a tissue piece or cultured cells and the like. These can be prepared by a method known per se. Examples of the cells to be prepared include fibroblast, myofibroblast, dendritic cell, keratinocyte, cardiac cell, oesophagus cell, myocyte, bone marrow cell, B lymphocyte, T lymphocyte, neutrophil, red blood cell, platelet, macrophage, monocyte, osteocyte, bone marrow cell, adipocyte, mesenchymal cell, epithelial cell, epidermal cell, endothelial cell, vascular endothelial cell and the like, but are not limited to these and those of ordinary skill in the art can appropriately prepare them according to the object. Examples of the tissue to be prepared include skin, oesophagus, lung, stomach, pancreas, liver, gall bladder, bile duct, small intestine, large intestine, kidney, bladder, prostate, uterus, ovary, blood vessel, bone marrow, brain, tongue, pharyngis and the like, but are not limited to these and those of ordinary skill in the art can appropriately prepare them according to the object.

For example, adult skin fibroblast collected from the non-human animal of the present invention (e.g., mouse) lacks expression of IKKβ under the culture conditions, inhibits activation of NFκB, and enhances deposition of collagen as in in vivo. While the fibroblast shows decrease in the expression and activity of MMP9, it shows increased expression of non-phosphorylated β-catenin, an active form thereof.

According to the present invention, it is possible to collect cells from the tissue or organ of a non-human animal obtained by the aforementioned method to prepare cultured cells (e.g., adult fibroblast etc.), co-culture the cells with antigen presenting cells, and use the aforementioned co-culture system to elucidate abnormal enhancement of the immune reaction, the mechanism of autoantibody production, and the like. Examples of the antigen presenting cell include dendritic cell, monocyte•macrophage, B cell and the like.

The culture temperature, $CO_2$ concentration and the like of co-culture can be appropriately determined by those of ordinary skill in the art. The culture temperature is, for example, 20° C.-50° C., more preferably 30° C.-40° C. The $CO_2$ concentration is, for example, about 1-10%, preferably about 5%. The medium to be used for the culture can be appropriately selected according to the cell type, it is, for example, MEM medium, DMEM medium, αMEM medium, IMDM medium, Eagle MEM medium, Ham's medium, RPMI1640 medium, Fischer's medium, McCoy's 5A medium or the like, and it is not limited to these. Furthermore, the medium can contain serum (e.g., FCS), serum replacement (e.g., KSR, albumin, transferrin, fatty acid, insulin, collagen precursor), fatty acid or lipid, amino acid, vitamin, growth factor, cytokine, antioxidant, 2-mercaptoethanol, pyruvic acid, buffering agent or inorganic salts and the like.

The antigen presentation capacity by co-culture of the cells (e.g., fibroblast) obtained in the present invention and antigen presenting cells can be evaluated by the method described in the below-mentioned Example.

Alternatively, it can be performed by a method known per se.

Screening Method

The present invention provides a screening method for a test substance, which characteristically uses the fibrotic non-human animal of the present invention or tissue or cultured cells and the like prepared from the non-human animal. Particularly, since the fibrotic non-human animal of the present invention shows fibrosis of various tissues or organs such as skin, oesophagus, lung, kidney and the like, tissues, the non-human animal or cultured cells and the like prepared from the non-human animal can be applied to screening for a prophylactic or therapeutic drug for fibrosis, elucidation of the mechanism of fibrosis, and development of a new treatment method for fibrosis and the like.

The method of screening for a substance for the prophylaxis and/or treatment of fibrosis of tissue of the present invention comprises (a) a step of administering a test substance to a non-human animal obtained by the present invention, and (b) a step of analyzing fibrosis of the tissue or organ of the aforementioned non-human animal. More specifically, it includes steps of administering a test substance to the aforementioned non-human animal and control group (control), measuring the levels of fibrosis, thickening, collagen deposition, expression of collagen I, TGFβ, β-catenin, and the like of the tissue or organ of the both animals, and comparing them, as well as a step of confirming the effect of the test substance based on the aforementioned comparison results.

The aforementioned administration can be performed by oral administration or parenteral administration. Examples of the oral administration include oral administration, sublingual administration and the like, examples of the parenteral administration include intravenous administration, intramuscular administration, subcutaneous administration, transdermal administration, transnasal administration, lung administration and the like, and those of ordinary skill in the art can appropriately determine them according to the object. In addition, those of ordinary skill in the art can also appropriately determine the dosing period, administration frequency, dose and the like thereof according to the kind of the test substance, the kind and body weight of the target animal, and the like.

Examples of the aforementioned tissue or organ include, but are not limited to, brain, tongue, pharyngis, skin, oesophagus, lung, mamma, stomach, pancreas, liver, gall bladder, bile duct, small intestine, large intestine, kidney, bladder, prostate, uterus, ovary, blood vessel, bone marrow and the like.

A substance for the prophylaxis and/or treatment of fibrosis can also be screened for by preparing a culture preparation product such as tissue, tissue fragment or cultured cells etc. from the non-human animal obtained in the present invention (i.e., a part of the living body of the non-human animal of the present invention). The screening method includes (a) a step of contacting a test substance with a tissue, tissue fragment or culture preparation product prepared from the non-human animal obtained in the present invention, and (b) a step of analyzing fibrosis in the aforementioned tissue, tissue fragment or culture preparation product. In more detail, it includes steps of contacting a test substance with the aforementioned tissue, tissue fragment or culture preparation product and a tissue, tissue fragment or culture preparation product to be the control, measuring the levels of fibrosis, thickening, collagen deposition, expression of collagen I, TGFβ, β-catenin, and the like in both tissues, tissue fragments or culture preparation products, and comparing them, as well as a step of confirming the effect of the test substance based on the aforementioned comparison results.

Furthermore, the present invention also encompasses a method including contacting the substance obtained by the aforementioned screening method with the non-human animal, cell or tissue of the present invention, and confirming the level of fibrosis.

In the aforementioned screening method, analyzing fibrosis refers to measurement and evaluation of the state of the level of fibrosis, whether it is decreased or suppressed, increased or enhanced, or no change of increase or decrease and the like. The measurement method may be a method known per se such as the aforementioned visual observation, histological analysis, biochemical analysis, image analysis and the like, and those of ordinary skill in the art can appropriately determined the method.

For the prophylaxis or treatment of fibrosis, it is preferable that the administration or contact with a test substance decreases or suppresses the level of fibrosis.

Since the fibrotic non-human animal of the present invention or a part of the living body thereof (e.g., adult fibroblast etc.) strongly reflects the pathology of scleroderma in human, the present invention also provides a method of screening for a substance for the prophylaxis and/or treatment of scleroderma by using the non-human animal. Particularly, since the fibrotic non-human animal of the present invention shows fibrosis in various tissues or organs, and produces a scleroderma patient-specific autoantibody, thus strongly reflecting the pathology of scleroderma, the non-human animal or cultured cells and the like prepared from the non-human animal can be applied to screening for a prophylactic or therapeutic drug for scleroderma, elucidation of the mechanism of scleroderma, and development of a new treatment method for scleroderma and the like.

For testing scleroderma, test of scleroderma patients can be applied besides the aforementioned measurement of fibrosis. For example, autoantibody test, skin biopsy, internal organ test and the like are performed. Examples of the autoantibody specific to scleroderma include anti-nuclear antibody, particularly, anti-Scl-70 antibody (anti-topoisomerase I antibody), anti-centromere antibody, anti-RNA polymerase III antibody, anti-nucleolar antibody and the like, and they can be detected by ELISA method and the like. As the antibody and kit used therefor, the aforementioned commercially available products and the like can be used as appropriate. Skin biopsy, internal organ test and the like are performed by a conventional method.

Furthermore, a candidate substance having a prophylactic and/or therapeutic effect on scleroderma can also be selected using, as an index, improvement of enlargement of right ventricle, hypertension, enlargement of spleen, suppression of infiltration of B and/or T cells into a skin lesion, suppression of activation of B cells and/or T cells in the spleen and the like, or increased expression and/or activity of MMP9 in fibroblasts in the living body, which are derived from a non-human animal, inhibition of expression of active β-catenin, inhibition of antigen presentation capacity (activation of T cells) when co-cultured with dendritic cell, increase in expression of p65 or NFκB activity and the like, as compared to those of the test substance non-administration group.

In the aforementioned methods, examples of the "test substance" include a substance desired to be confirmed as to the effectiveness as a prophylactic drug or a therapeutic drug for fibrosis or scleroderma, and a substance which is a therapeutic drug for other diseases and required to be confirmed as to an influence (e.g., toxicity) on fibrosis or scleroderma. Examples of the substance include low-molecular-weight compound, polymer compound, protein (cytokine, chemokine, antibody etc.), nucleic acid (DNA, RNA etc.), virus, compound library prepared by combinatorial chemistry techniques, random peptide library produced by solid phase synthesis and phage display method, natural components derived from microorganism, animals and plants, marine organism and the like, and the like. Such substance can be appropriately determined by those of ordinary skill in the art.

Composition

A substance obtained by the above-mentioned screening method can be a candidate substance effective for the prophylaxis or treatment of fibrosis or scleroderma. Therefore, the present invention also provides a pharmaceutical composition or preparation comprising the substance as an active ingredient. The pharmaceutical composition or preparation can contain any carrier below.

Of any carriers, examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropyl-starch, sodium-glycol-starch, sodium hydrogen carbonate, calcium phosphate, calcium citrate and the like, lubricants such as magnesium stearate, AEROSIL®, talc, sodium lauryl sulfate and the like, aromatics such as citric acid, menthol, glycyllysin ammonium salt, glycine, orange powder and the like, preservatives such as sodium benzoate, sodium bisulfite, methylparaben, propylparaben and the like, stabilizers such as citric acid, sodium citrate, acetic acid and the like, suspension such as methylcellulose, polyvinylpyrrolidone, aluminum stearate and the like, dispersing agents such as surfactant and the like, diluent such as water, saline, orange juice and the like, base wax such as cacao butter, polyethylene glycol, kerosene and the like, and the like.

Examples of the preparation preferable for oral administration include a liquid obtained by dissolving an effective amount of a substance in a dilution liquid such as water, saline, a capsule containing an effective amount of a substance as a solid or granule, sachet or tablet, a suspension wherein an effective amount of a substance is suspended in a suitable dispersing medium, an emulsion wherein a solution of an effective amount of a substance is dispersed and emulsified in a suitable dispersing medium, powder, granule and the like.

Examples of the preparation preferable for parenteral administration (intravenous injection, subcutaneous injection, muscular injection, topical injecting etc.) include aqueous or non-aqueous isotonic and aseptic injection liquids, which may further contain antioxidant, buffer, bacteriostatic, isotonic agent and the like. The preparation can be encapsulated in a container such as ampoule and vial by a unit dose or plural doses. In addition, an active ingredient and a pharmaceutically acceptable carrier may be freeze-dried and preserved in a state requiring dissolving or suspending in a suitable aseptic vehicle immediately before use.

In the present invention, it was found that IKKβ binds directly with β-catenin and regulates expression of the active molecule thereof. Accordingly, the present invention also provides a method of screening for a substance for the prophylaxis and/or treatment of fibrosis and/or scleroderma, which uses, as an index, whether or not a test substance inhibits interaction (binding) of IKKβ and β-catenin. As the screening method, for example, protein interaction analysis methods known per se such as immunoprecipitation assay (pull-down assay), two-hybrid method and the like can be applied.

Transgenic Non-Human Animal

In another embodiment, the present invention further provides a transgenic (Tg) non-human animal that overexpresses IKKβ gene in a myofibroblast- and/or smooth muscle cell-specific manner. The Tg animal can be obtained by introducing an expression cassette wherein IKKβ gene is inserted under regulation of a myofibroblast- and/or smooth muscle cell-specific promoter (e.g., SM22α promoter), which is similar to those mentioned above, by a method known per se (e.g., microinjection into fertilized egg etc.). The Tg animal stably retains the IKKβ gene in a state permitting myofibroblast- and/or smooth muscle cell-specific expression. In adult fibroblasts derived from the Tg animal, expression and activity of MMP9 markedly increase compared to the wild-type, but expression of active β-catenin decreases.

These findings suggest that myofibroblast- and/or smooth muscle cell-specific overexpression of IKKβ gene can promote degradation of collagen, and suppress fibrosis of tissue. Accordingly, the phenotype of the Tg animal suggests the possibility of a myofibroblast- and/or smooth muscle cell-specific IKKβ substitution therapy.

Scleroderma Patients

The findings obtained from the non-human animal of the present invention also provides an evaluation method of a treatment effect for scleroderma patients. As described in the below-mentioned Examples, scleroderma patients show strong suppression of the expression of IKKβ due to the stimulation by IL-1β, and inhibition of the expression of p65 and activity of NFκB. Therefore, the treatment effect can be judged by performing, before and after treatment, for example, biopsy, blood sampling and the like for scleroderma patients, preparing fibroblast and the like, measuring expression of IKKβ and/or p65, nuclear translocation of p65, activity of NFκB and the like in the cells by a method known per se, and comparing them before and after the treatment. Expression of IKKβ, expression and nuclear translocation of p65, and activity of NFκB can be measured by subjecting cellular or nuclear extracts of fibroblasts and the like to ELISA, EMSA, Western blotting, reporter gene assay and the like.

Also, since the suppression of the expression of IKKβ by IL-1β stimulation in fibroblasts derived from scleroderma patients was mitigated by a pre-treatment with a proteasome inhibitor, the present invention can also provide novel prophylaxis and/or treatment of scleroderma, which is based on the suppression of degradation of IKKβ and activation of NFκB pathway, due to the inhibition of proteasome.

The present invention is explained in more detail by referring to the following Examples. Examples merely show exemplification of the present invention, and do not limit the scope of the present invention in any way.

EXAMPLES

Antibody and Reagent

The antibodies and reagents used in the Examples were as follows.

Polyclonal anti-IKKβ antibody (Millipore), polyclonal anti-Sm22α (another name TAGLN) antibody (Lifespan Bioscience), polyclonal anti-MMP9 antibody (Abnova), GAPDH (Cell Signaling Technology, hereinafter to be referred to as "CST"), TGF (CST), p65 antibody (CST), anti-β-catenin antibody (CST), anti-active β-catenin antibody (Millipore), anti-PNA (Vector Laboratories Inc., Burlingame, Calif., USA) were used. In addition, commercially available following primers, TGFβ, CTGF, CollagenI and MMP9 (Applied Biosystems (trade mark)) were used to perform qRT-PCR. NE-PER nuclear protein, cytoplasmic protein separation extraction kit (Thermo Scientific) was used to extract nuclear protein. RNAaqueous (trade mark) kit (Applied Biosytems (trade mark)) was used to isolate RNA, and TaqMan (registered trade mark) Gene Expression Assays kit (Applied Biosytems (trade mark)) was used to measure gene expression level. As a proteasome inhibitor, MG132 (CAS registration No.; 133407-82-6) was used.

The primers used for TaqMan (registered trade mark) Gene Expression Assays are shown in Tables 1-3.

TABLE 1

| Mouse | | |
|---|---|---|
| Gene Name | AssayID | |
| matrix metallopeptidase 2 | Mm00439498_m1 | MMP2 |
| matrix metallopeptidase 9 | Mm00442991_m1 | MMP9 |
| collagen, type I, alpha 1 | Mm00801666_g1 | Colagen1A1 |
| connective tissue growth factor | Mm01192933_g1 | CTGF |
| transforming growth factor, beta 1 | Mm01178820_m1 | TGFb |

TABLE 2

| Human | | |
|---|---|---|
| Gene Name | AssayID | |
| v-rel reticuloendotheliosis viral oncogene homolog A (avian) | Hs01042010_m1 | p65 |

TABLE 3

| Gene Symbol | ABI Assay ID | RefSeq ID |
|---|---|---|
| Mmp2 | Mm00439498_m1 | NM_008610.2 |
| Mmp9 | Mm00442991_m1 | NM_013899.2 |
| Col1a1 | Mm00801666_g1 | NM_007742.3 |
| TGFb | Mm01178820_m1 | NM_011577.1 |
| Tagln | Mm00441661_g1 | NM_011526.5 |

Statistical Analysis

For the statistical analysis in the present invention, t-test of 2 samples was performed, and $P<0.05$ was judged to show a significant difference. The numerical values in Figures and Tables show mean±standard deviation. When the independence was rejected by the Kolmogorov-Smirnov test, the Wilcoxon-Mann-Whitney test was performed. In Figs., * shows $p<0.05$,  shows $p<0.01$, * shows $p<0.005$, and **** shows $p<0.001$.

Example 1

Preparation of Mouse Lacking IKKβ Gene in a Myofibroblast•Smooth Muscle Cell-Specific Manner A known IKKβ$^{flox/flox}$ mouse and an Sm22α-Cre$^+$ mouse (Science (2003), vol. 300, p. 329-332) were crossed to give hetero zygous mouse IKKβ$^{flox/wt}$ Sm22α-Cre$^{+/-}$ mouse. The aforementioned mouse and an IKKβ$^{flox/flox}$ mouse were crossed to give IKKβ$^{flox/flox}$ Sm22α-Cre$^{+/-}$ mouse (hereinafter to be referred to as KO mouse) and IKKβ$^{flox/flox}$ Sm22α-Cre$^{-/-}$ mouse (hereinafter to be referred to as WT mouse). KO mouse was born at a ratio following the Mendelian rule, and the growth thereof such as body weight profile and the like was not different from that of WT mouse. The KO mouse in the present invention was obtained by crossing mice of pure line animal lineage C57BL/6.

Figures 1, 2:
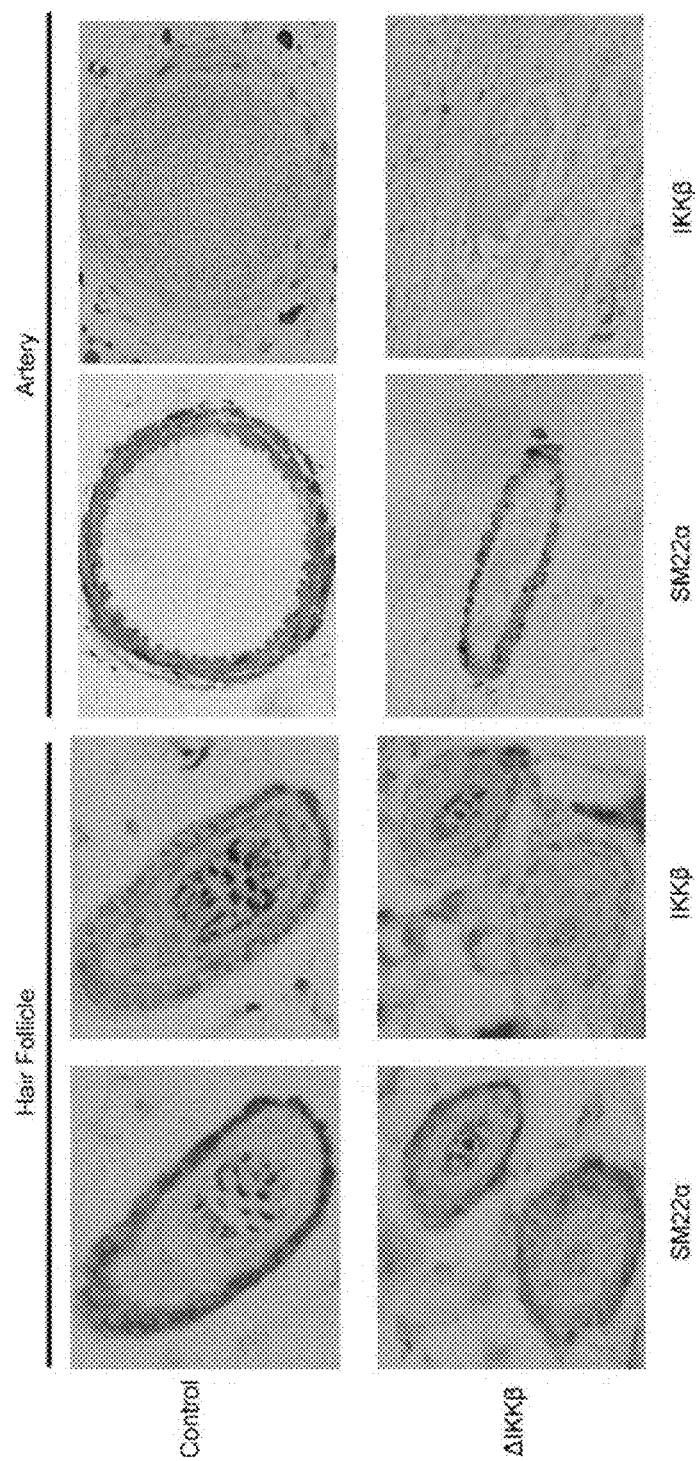
Figure 2:
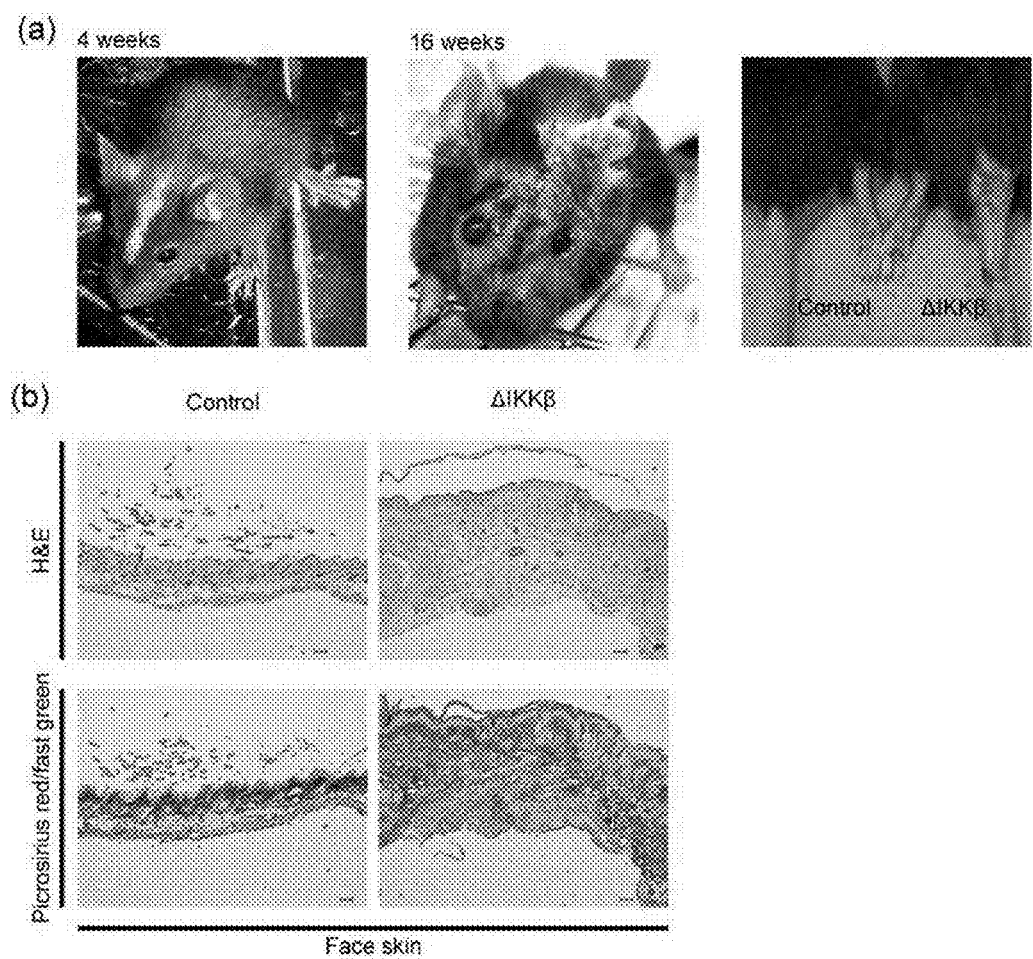

In KO mouse, lack of IKKβ was verified by immunostaining. Immunostaining was performed by the following method. A section after deparaffinization treatment and antigenicity retrieval was incubated in 0.3% hydrogen peroxide-methanol for 30 min, and the section was reacted with a diluted primary antibody at 4° C. overnight. Thereto was applied a diluted biotin-labeled secondary antibody and the mixture was reacted at room temperature for 60 min, ABC reagent was applied, and the mixture was reacted at room temperature for 30 min. Furthermore, DAB reagent (TBST, dilut 1:10 at pH 7.6) added with 3% hydrogen peroxide (1:125) was applied, and the mixture was reacted for 1 min. For counterstaining, hematoxylin was used. The results are shown in FIGS. 1-1 and 1-2. FIG. 1-1 shows that the growth of KO mouse is not different from that of WT mouse. FIG. 1-2 shows that the aforementioned KO mouse lacks IKKβ and WT mouse has IKKβ in hair follicle periphery myofibroblasts and vascular smooth muscle cells.

Example 2

Fibrosis of Tissue in IKKβ KO Mouse (1) Fibrosis of Skin

In the mice obtained in Example 1, 4-week-old KO mouse showed hairless skin lesion in a part of the head (FIG. 2(*a*), left). In contrast, the aforementioned lesion was not observed in WT mouse. In average 16-week-old KO mice, skin hardening accompanying erosion was highly frequently observed on the head and tail (FIG. 2(*a*), middle and right). Therefore, histological observation was also performed. For skin tissue staining, 2-4 μm serial sections of paraffin-embedded tissue were stained with hematoxylin-eosin (H&E). To evaluate collagen amount and collagen tissue, deparaffinized section was stained with picrosirius red/fast green. As a result, marked thickening of epidermis and dermis, and marked accumulation of collagenous fiber were histologically observed in KO mouse. In contrast, the aforementioned lesions were not observed in WT mouse (FIG. 2(*b*)).

Figure 3:
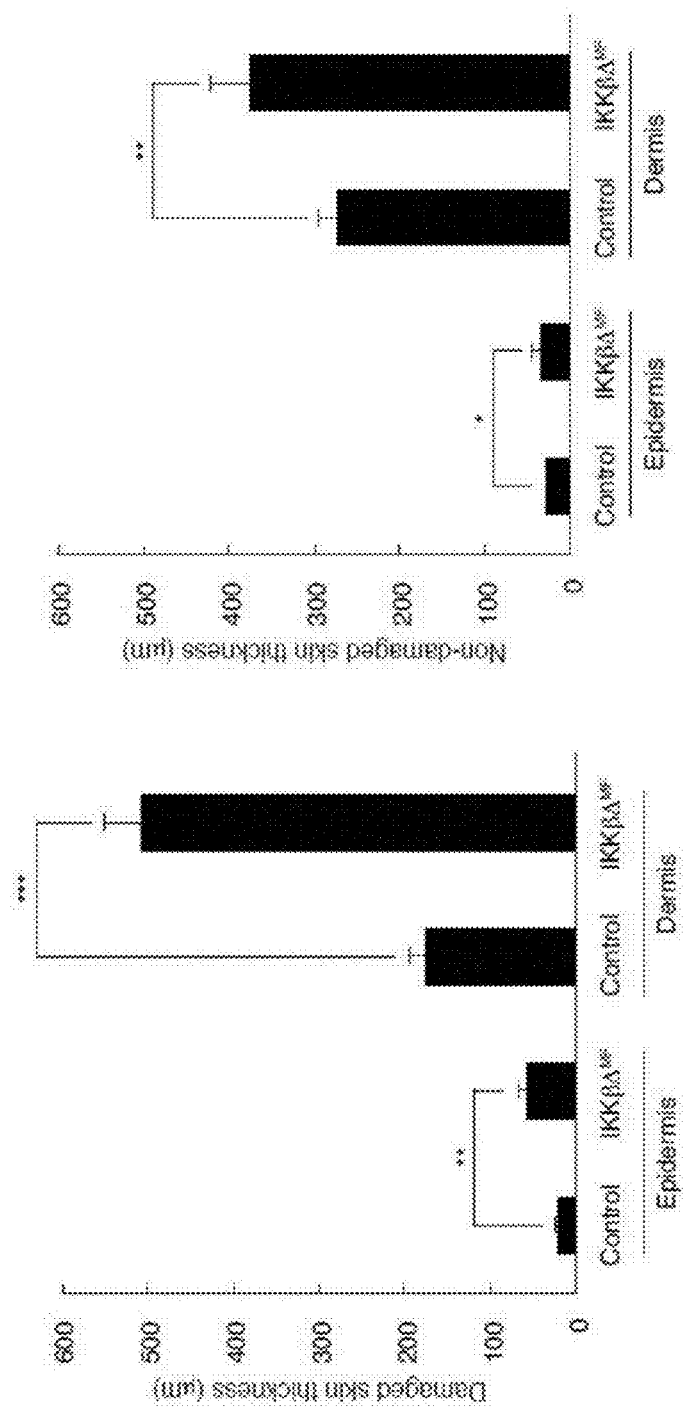
FIG. 3 shows the measurement results of the thickness of the skin of the lesion part (left) and non-lesion part (right) of the knockout mouse (IKKβ$^{ΔMF}$) and wild-type mouse (control). Knockout mouse showed deposition of collagen fiber not only in the lesion part but also in the non-lesion part of the facial and tail skin.

The skin thickness was measured by the following method. The skin of face or tail was collected with a 6 mm biopsy punch, embedded in paraffin to give 4 μm sections, which were hematoxylin-eosin (H&E) stained and subjected to microscope observation. Photographs were taken at ×200 magnification. The results are shown in FIG. 3. Thickening was found not only in the skin of lesion (left) but also the skin of apparently normal non-lesion part (right), and both in epidermis and dermis, and marked deposition of collagen was observed in dermis. Such tendency was biased and 3-4 times higher in female mouse compared to male mouse. While SM22α is also expressed in vascular smooth muscle cells, morphological change or deposition of collagen was not found in the aorta.

(2) Lesion in Oesophagus

Figures 1, 4:
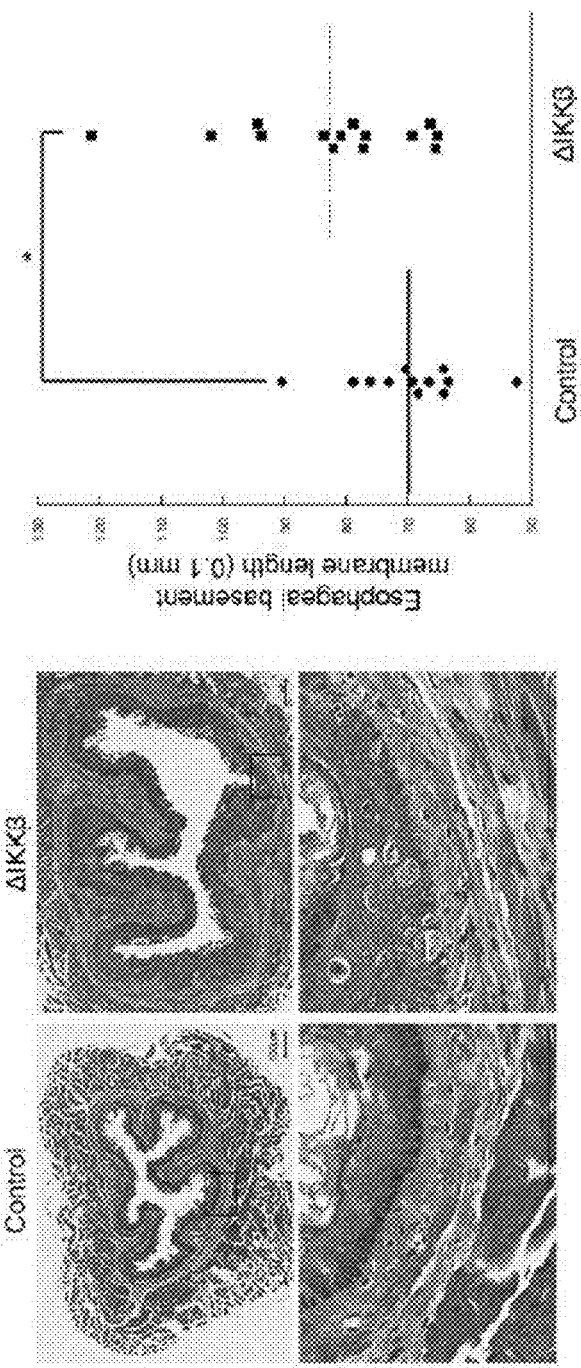
Figures 2, 4:
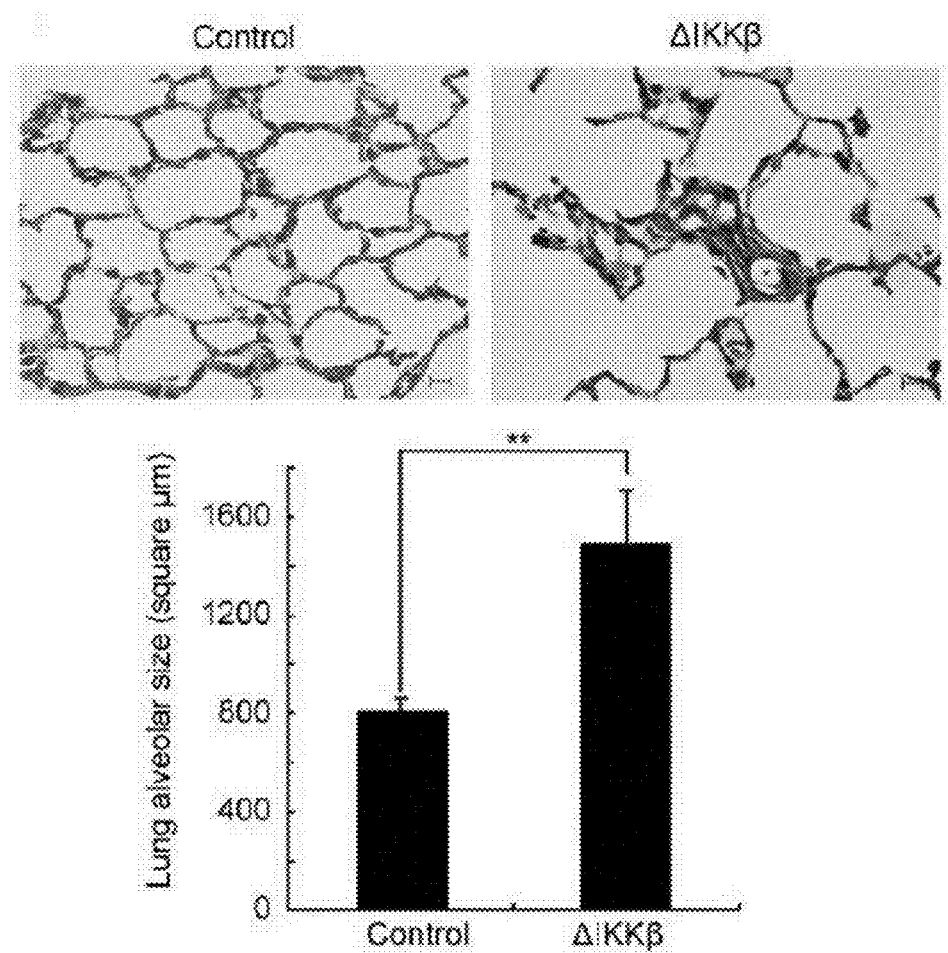
Figures 3, 4:
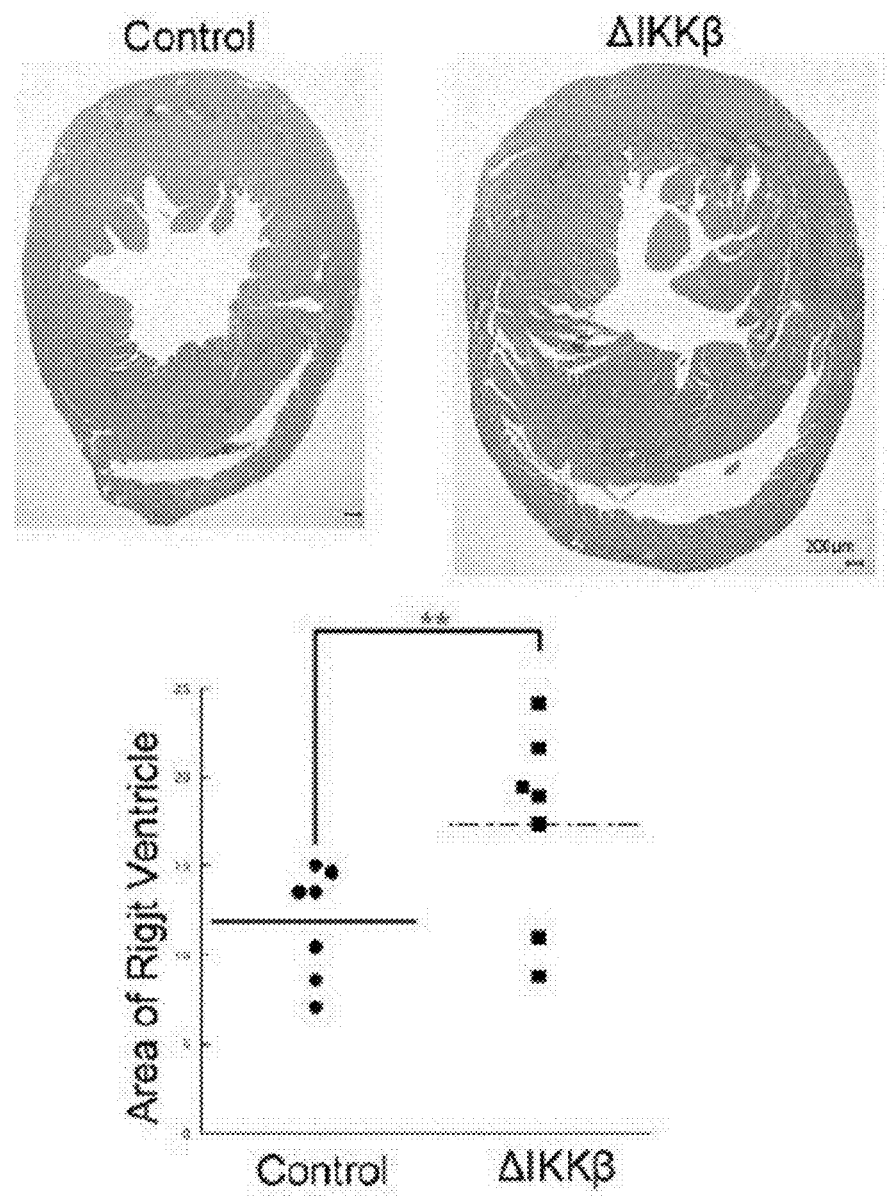
Figure 4:
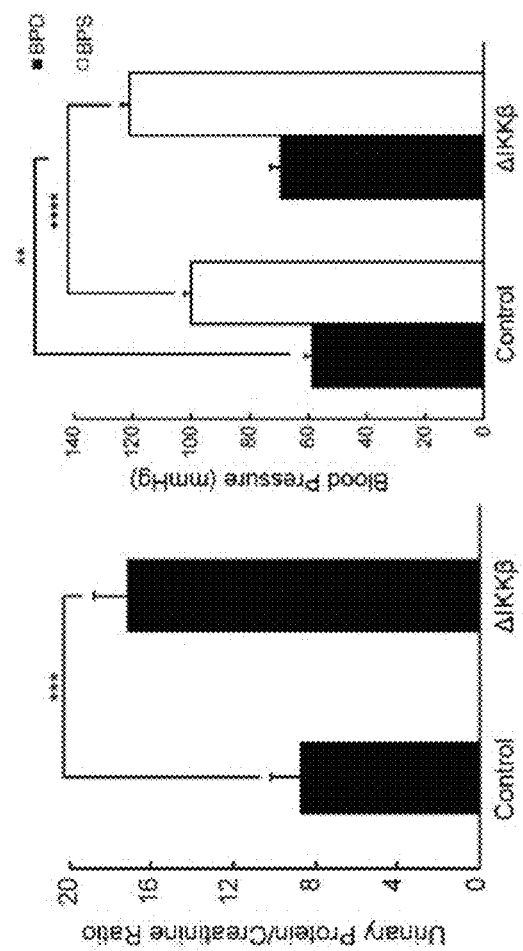
Figure 4:

The oesophagus of the mice obtained in Example 1 was observed. A paraffin-embedded, 4 μm section of oesophagus was stained with Masson's trichrome, and observed under a microscope. The length of the muscularis mucosa was measured and analyzed using Image J software. As a result, substitution of collagenous fiber for smooth muscle below mucosa in lower oesophagus and expansion of the oesophagus were found in KO mouse. In contrast, the aforementioned lesion was not found in WT mouse. The results are shown in FIG. 4-1.

(3) Lesion in Lung and Heart

The lung of the mice obtained in Example 1 was observed. Paraffin-embedded 4 μm sections of lung and heart were subjected to hematoxylin-eosin (H&E) staining and Masson's trichrome staining, and observed under a microscope. The size of alveolus was measured and analyzed using Image J software. As a result, accumulation of collagenous fiber and enlargement of alveolus were found in the lung of KO mouse. In contrast, the aforementioned lesions were not found in WT mouse. The results are shown in FIG. 4-2. Furthermore, expansion of right ventricle suggestive of lung hypertension was found in KO mouse. In contrast, the aforementioned lesions were not found in WT mouse. The results are shown in FIG. 4-3.

(4) Lesion in Kidney

The kidney of the mice obtained in Example 1 was observed. The kidney tissue was stained with picrosirius red/fast green by the aforementioned method. In addition, urine was collected from the mouse over 24 hr, and the total protein in the urine and creatinine concentration were measured. The systolic phase (BPS) and diastolic phase (BPD) blood pressures were measured by an automatic blood pressure measurement apparatus (MK-2000A, Muromachi, Tokyo, Japan) by using the tail-cuff method. As a result, stenosis of afferent and efferent glomerular arteries and accumulation of collagenous fiber in the kidney, and increase in urinary protein and hypertension seemingly caused by the aforementioned lesion were found in the KO mouse. In contrast, the aforementioned lesions were not found in WT mouse. The results are shown in FIG. 4-4.

(5) Accumulation of Collagen I

Figure 5:
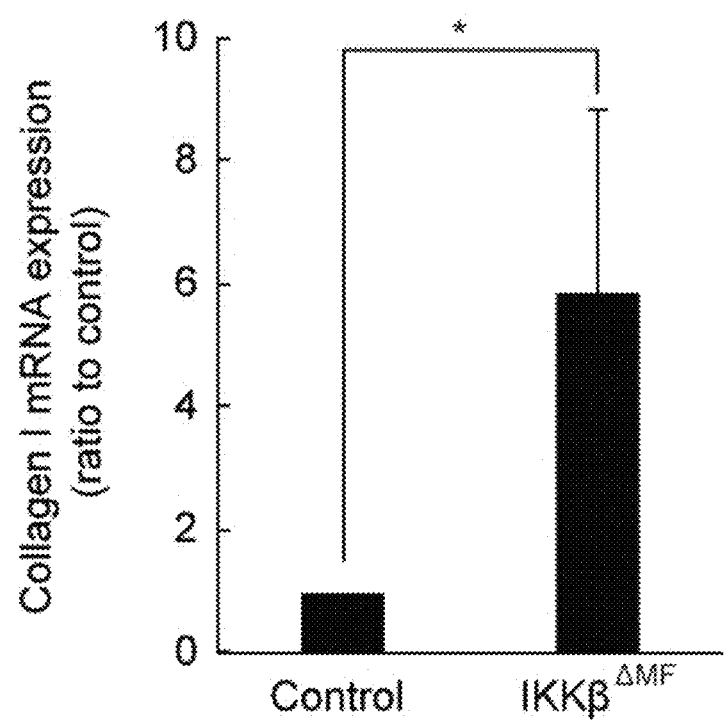
FIG. 5 shows an increase ratio of the collagen I mRNA level of the skin of knockout mouse (IKKβ$^{ΔMF}$) and wild-type mouse (control) as measured by qRT-PCR relative to control as 1. The skin of knockout mouse shows about 6 times higher increase in the collagen I level as compared to the control.

The mRNA level of collagen I in the skin of the mice obtained in Example 1 was verified by the qRT-PCR method. The aforementioned commercially available primers and kit were used. KO mouse showed about 6 times higher increase in collagen I mRNA as compared to WT mouse. The results are shown in FIG. 5.

Example 3

Figures 1, 6:
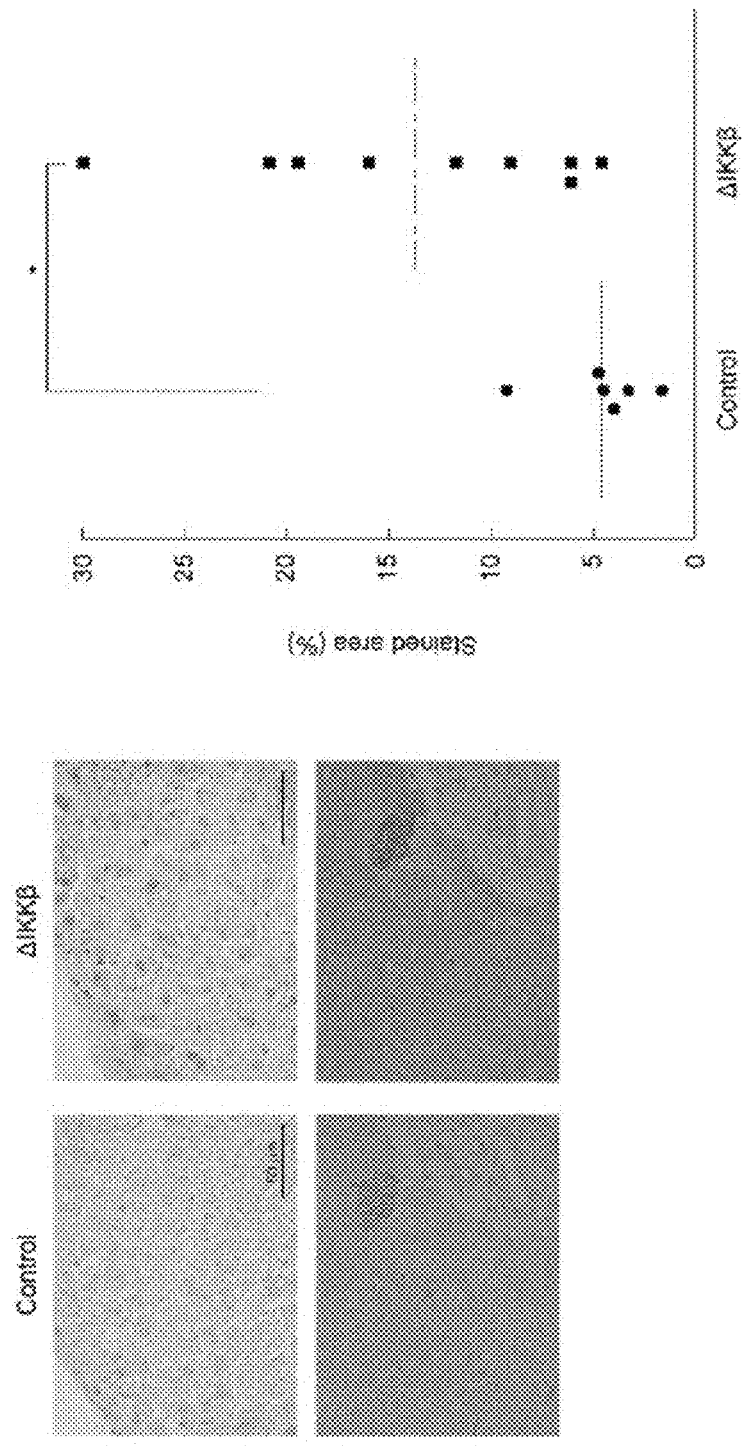
Figures 2, 6:
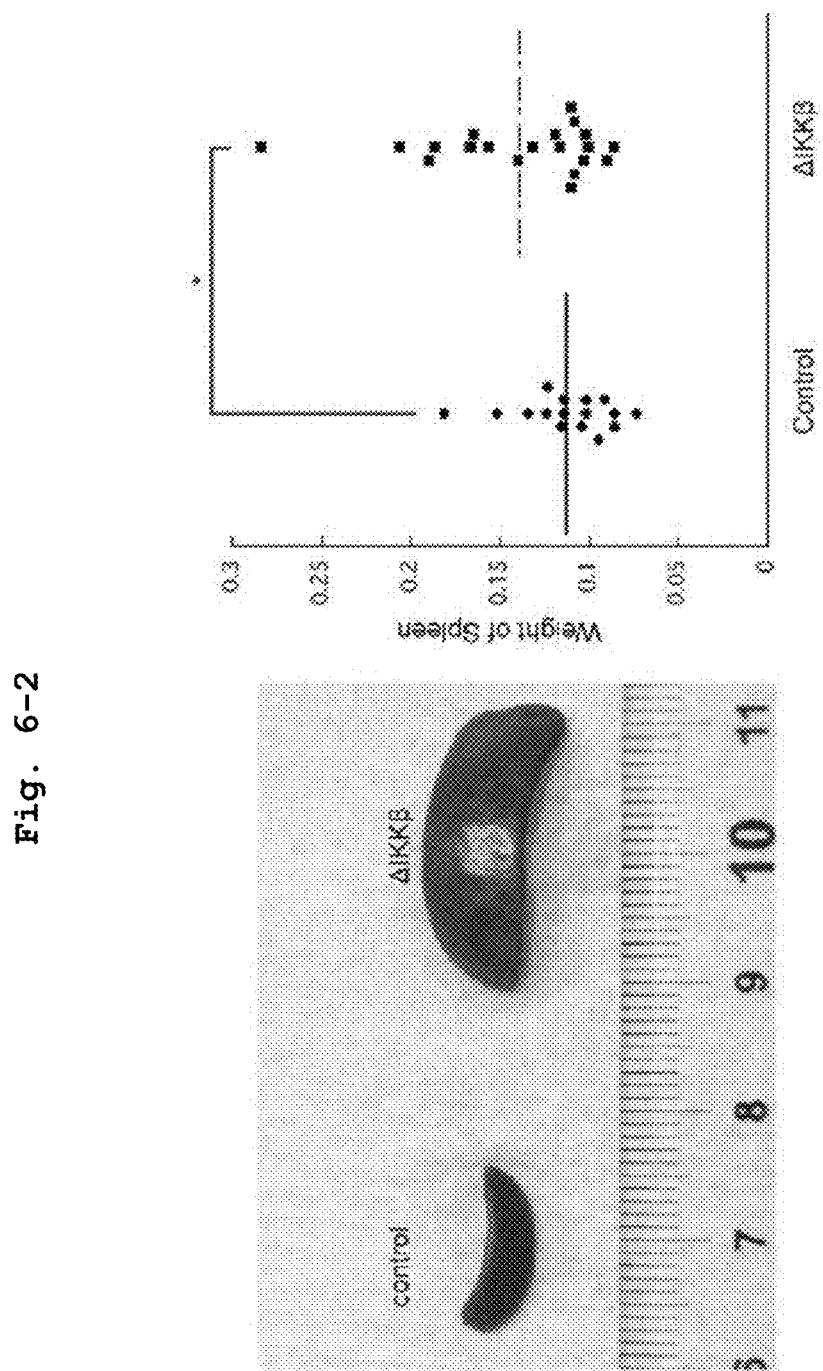
Figures 3, 6:
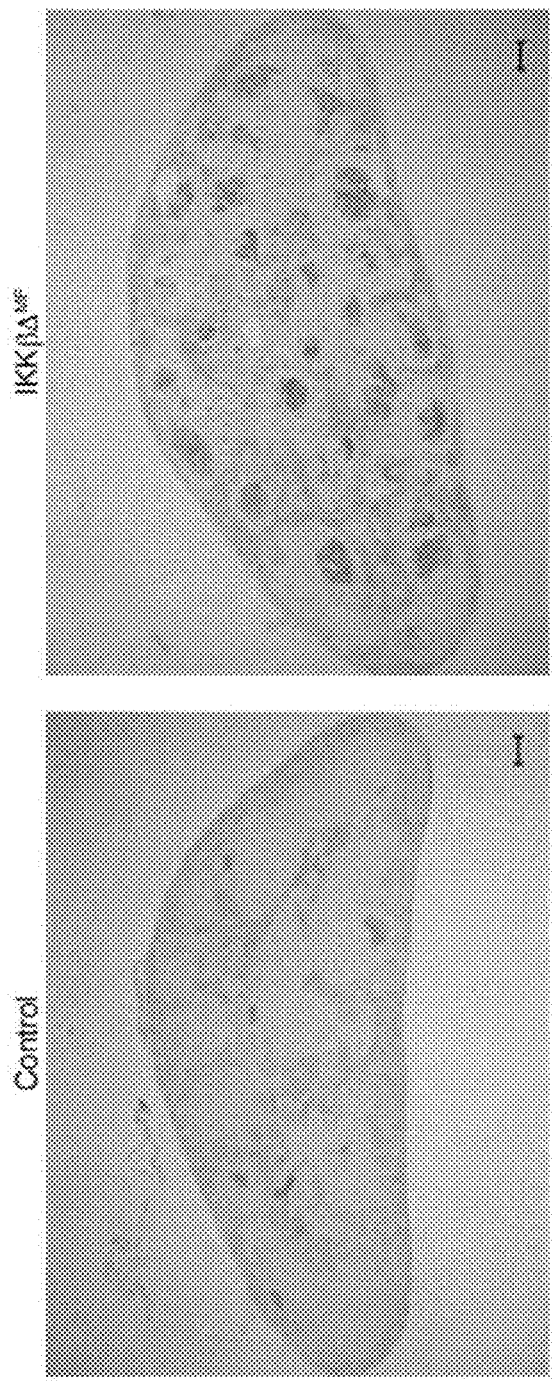

Production of Autoantibody in Mouse Lacking IKKβ Gene in a Myofibroblast•Smooth Muscle Cell-Specific Manner (1) Nucleus and Cytoplasm and Lesion of Spleen The presence of autoantibody in the mice obtained in Example 1 was examined. The same normal hepatic tissue was incubated with each of the sera (20-fold diluted) of WT and KO mice, and DAB staining was performed by the aforementioned method. As a result, nuclear and cytoplasmic staining was found in KO mouse, thus suggesting the presence of autoantibody (FIG. 6-1).

Furthermore, the spleen was isolated from the both mice and observed. As a result, enlargement of spleen was found in KO mouse, thus suggesting an abnormal autoimmune state (FIG. 6-2). Moreover, B cell was activated in the spleen of the KO mouse (FIG. 6-3). Also, infiltration of CD45 positive B or T cells as in scleroderma patients was found in the skin lesion of the KO mouse. In contrast, none of the aforementioned lesions was found in WT mouse (FIGS. 6-1-6-3).

(2) Production of Autoantibody Specific to Scleroderma

Figure 7:
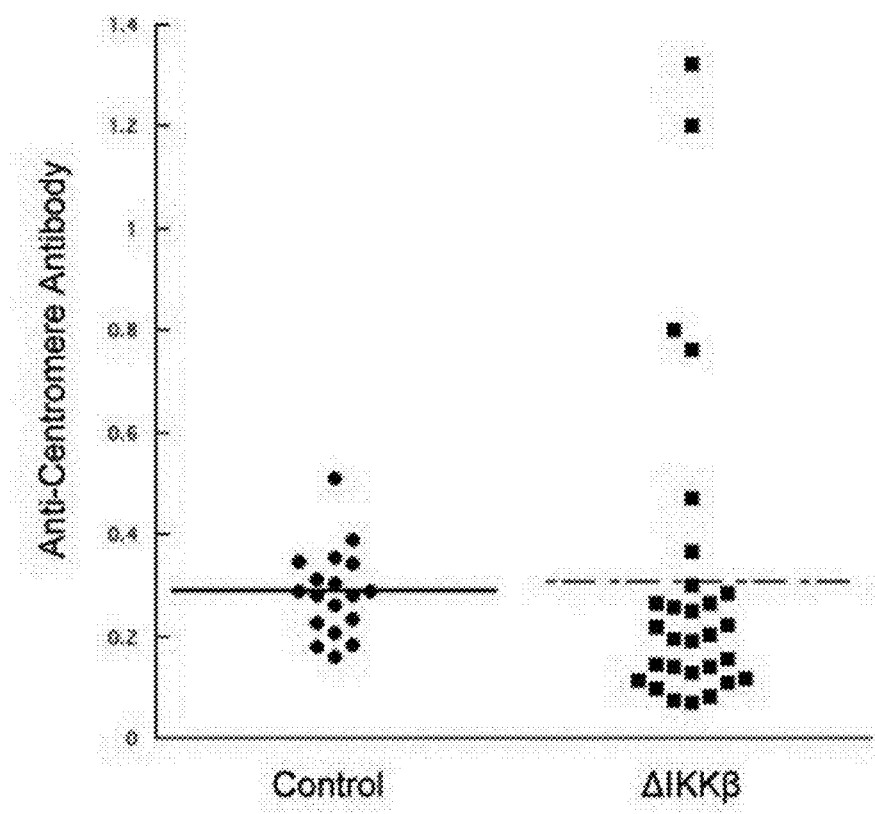
FIG. 7 shows the presence of an anti-centromere antibody in the knockout mouse (ΔIKKβ). Knockout mouse showed the presence of an autoantibody specific to scleroderma patients.

In addition, the presence or absence of anti-centromere antibody, which is an autoantibody specific to scleroderma, in the aforementioned mice was examined by the ELISA method. KO mouse showed a significantly high value of anti-centromere antibody as compared to WT mouse. The results are shown in FIG. 7.

Example 4

Expression of Cytokine and Collagen in IKKβ KO Mouse

To explore the mechanism of the phenotype of KO mouse found in Examples 2 and 3, protein in the skin tissue of the mice obtained in Example 1 was measured by Western blot method and mRNA was measured by the qRT-PCR method.

Figure 8:
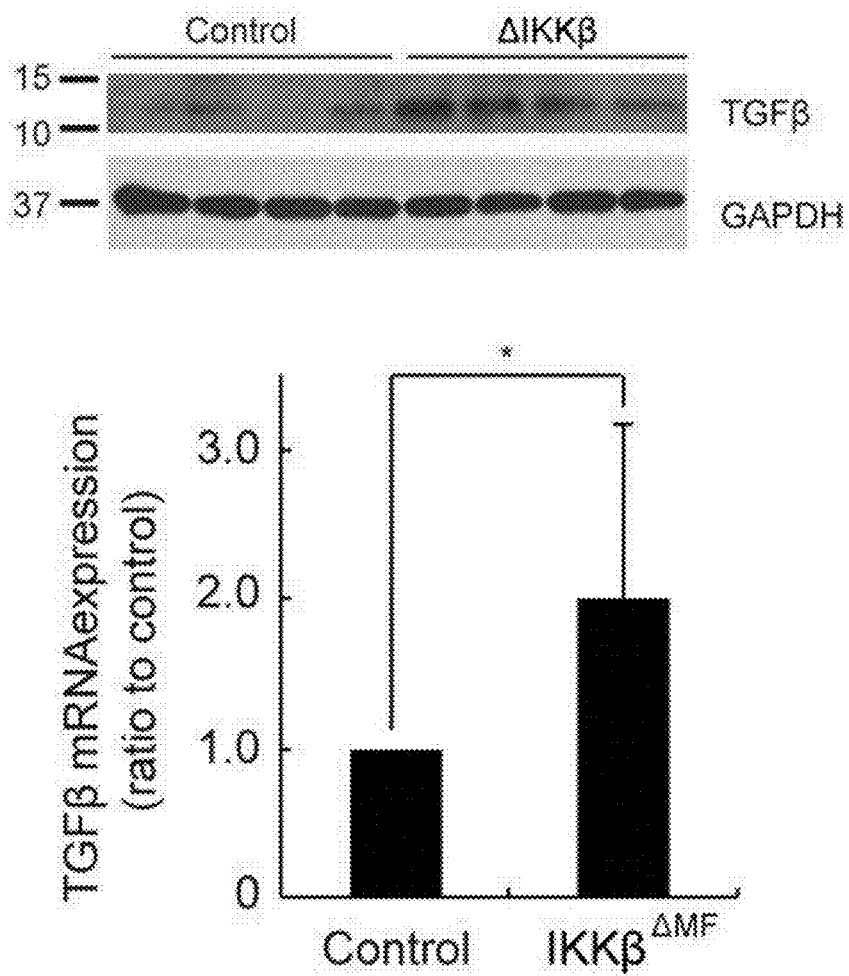
FIG. 8 shows expression of TGF protein (upper) and mRNA (lower) in the skin of knockout mouse (ΔIKKβ, IKKβ$^{\Delta MF}$). An increase in TGFβ, which is observed in scleroderma patients, was also observed in both protein and mRNA.

As a result, an increase in TGFβ, which is found in scleroderma patients, was found in both protein and mRNA. The results are shown in FIG. 8.

As an in vitro experiment system, fibroblasts (AFbs) were prepared from the skin tissue of adult mouse. Since AFbs express SM22α by plate culture, they already lacked IKKβ before induction of myofibroblast differentiation by TGFβ stimulation. Due to the lack of IKKβ, activation of NFκB was inhibited in AFbs. As observed in vivo, the deposition of collagen was also enhanced in the cultured cells of AFbs.

Using AFbs, protein and RNA were extracted from the cell. The expression level of mRNA of a regulatory factor of the accumulation and degradation of various collagens was examined by the qRT-PCR method. In all experiments, mRNA expression of MMP9 was significantly suppressed compared to the wild-type (FIG. 9-1(*a*)). Then, the activity of MMP9 protein was verified by the gelatin zymography method (FIG. 9-1(*b*)). As a result, the activity of MMP9 markedly decreased in AFbs derived from KO mouse as compared to WT mouse, which was considered the mechanism of collagen accumulation (FIG. 9-1(*b*)).

Figures 2, 9:
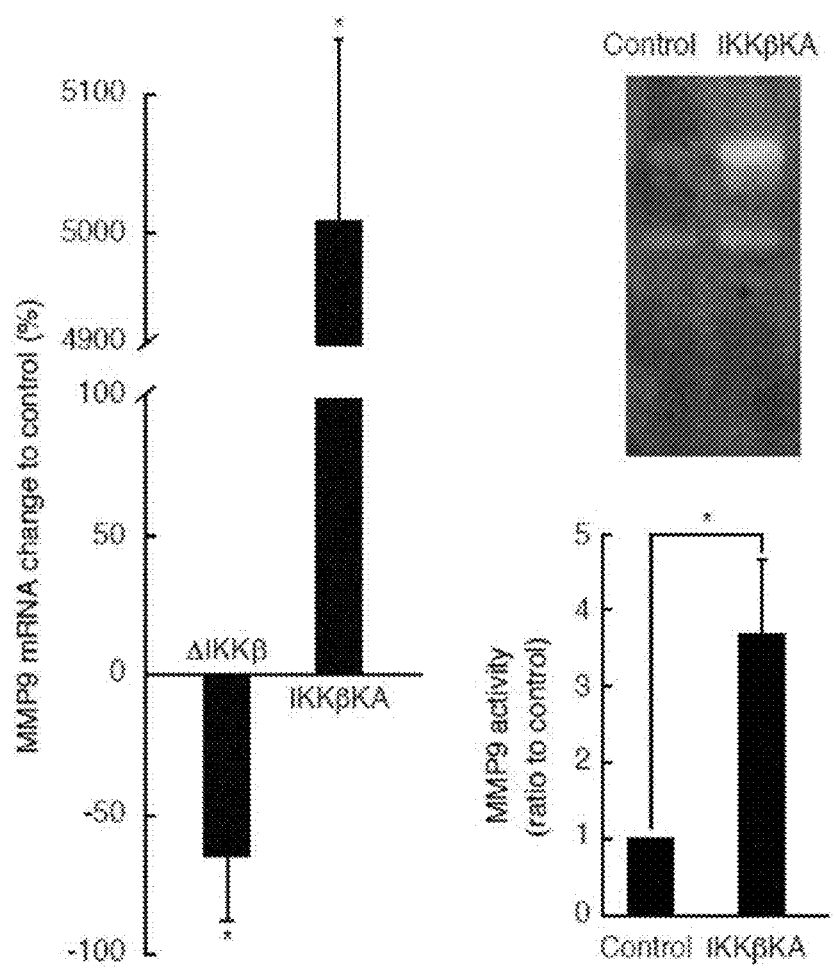
Figures 3, 9:
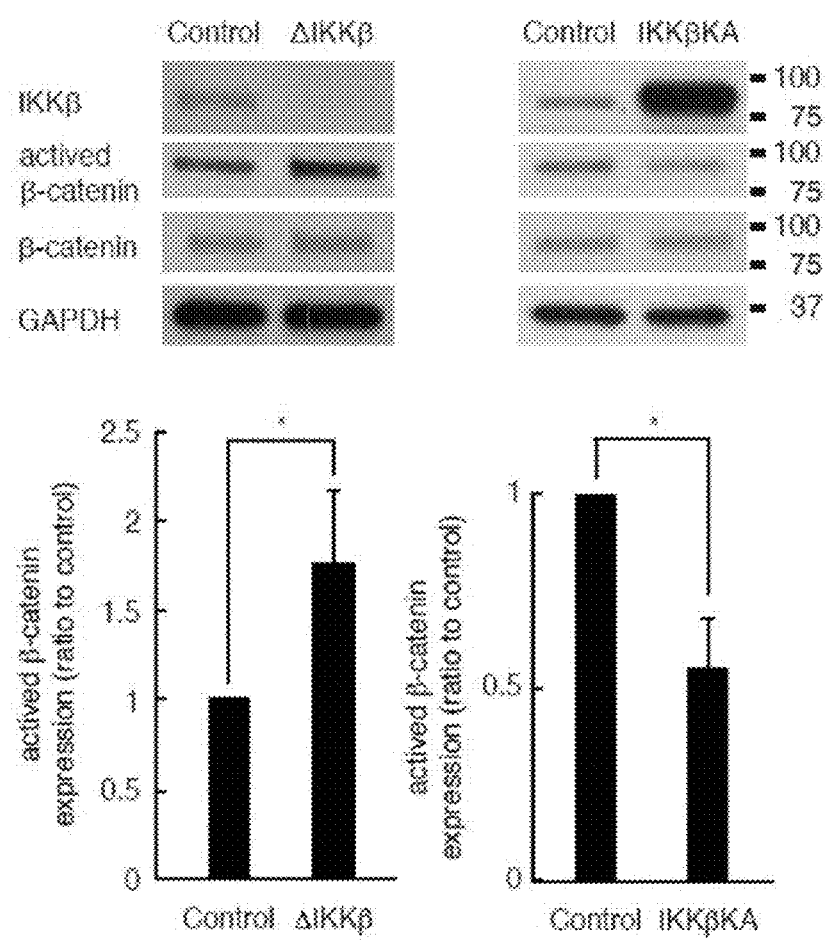
Figures 4, 9:
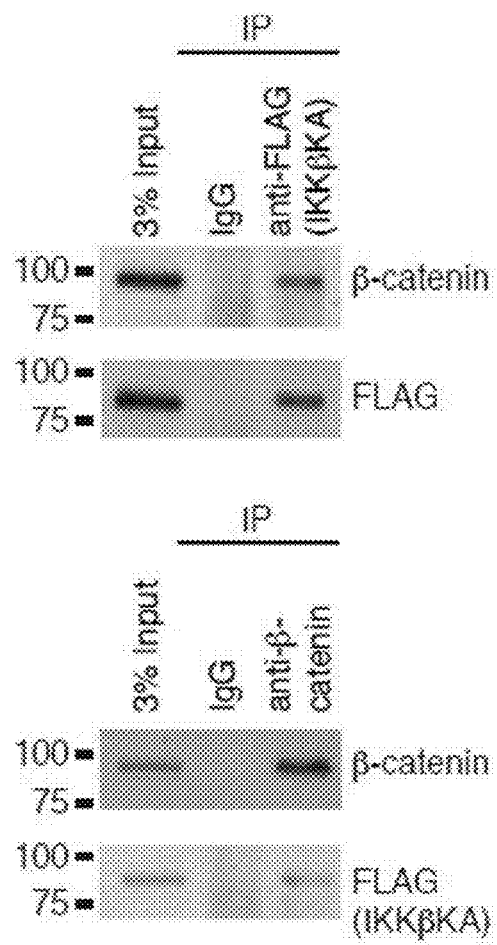

Furthermore, IKKβKA$^{MF}$ mouse that overexpresses kinase active IKKβ under SM22α promoter was produced, and fibroblasts were collected from an adult mouse thereof. In the same manner as above, mRNA level and activity of MMP9 were verified from the cell. As a result, mRNA level and activity of MMP9 markedly increased as expected. The results are shown in FIG. 9-2.

On the other hand, the expression of β-catenin considered to be involved in fibrosis was verified. As a result, the expression of active β-catenin markedly increased in IKKβKO mouse, whereas it was markedly suppressed in the IKKβKA$^{MF}$ mouse. The results are shown in FIG. 9-3. The results of the binding of IKKβ and β-catenin are shown in FIG. 9-4. IKKβKA$^{MF}$ fibroblast lysate (1 mg) was incubated with 1 µg of control IgG, anti-β-catenin antibody or anti-FLAG antibody overnight at 4° C., 25 µL Protein G Sepharose (GE Healthcare) was added and the mixture was shaken at 4° C. for 1 hr. The precipitate was washed 3 times with cell lysis buffer and once with Tris (pH 7.5) buffer, eluted with SDS sample buffer, and detected by immunoblotting using anti-β-catenin antibody or anti-FLAG antibody. As a result, it was shown that IKKβ and β-catenin directly interact.

Example 5

T Cells Activity in IKKβ KO Mouse

Myofibroblasts were prepared from the mice obtained in Example 1, and co-cultured with dendritic cells obtained from normal mouse. Culture was performed under the conditions of 37° C., 5% $CO_2$, and ovalbumin was used as an antigen. The growth of OVA specific T cells added was measured using [$^3$H]thymidine incorporation as an index, and the T cell proliferation capacity was determined.

Figure 10:
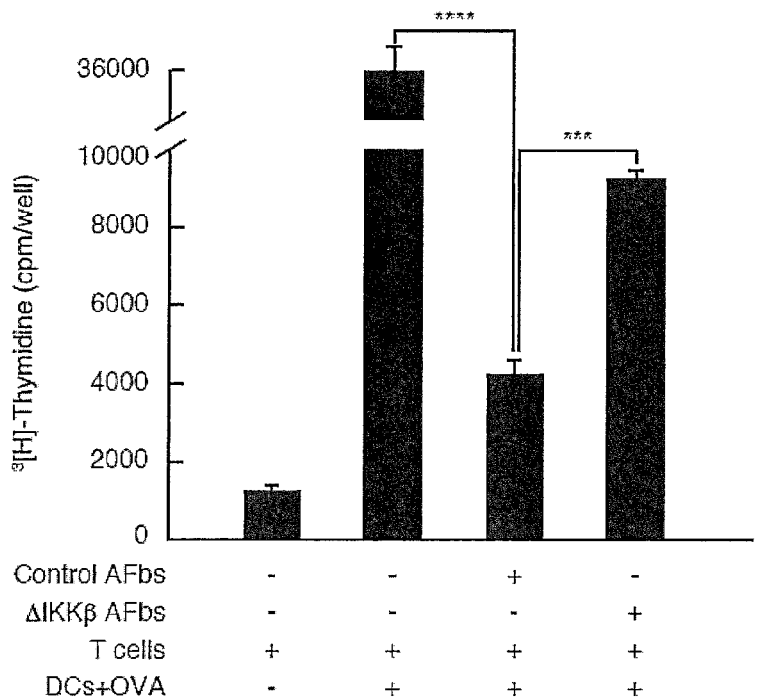
FIG. 10 shows the results of the measurement of an increase in the OVA specific T cells by using [$^3$H]thymidine incorporation as an index, when myofibroblast (AFbs) was prepared from adult knockout mouse (ΔIKKβ) and wild-type mouse (control), co-cultured with dendritic cell obtained from normal mouse, and ovalbumin (OVA) was used as an antigen. The myofibroblast of wild-type mouse strongly suppressed T cell stimulation by antigen presentation, whereas in the co-culture with myofibroblast of knockout mouse, T cell stimulation by antigen presentation recovered.
Figure 10:
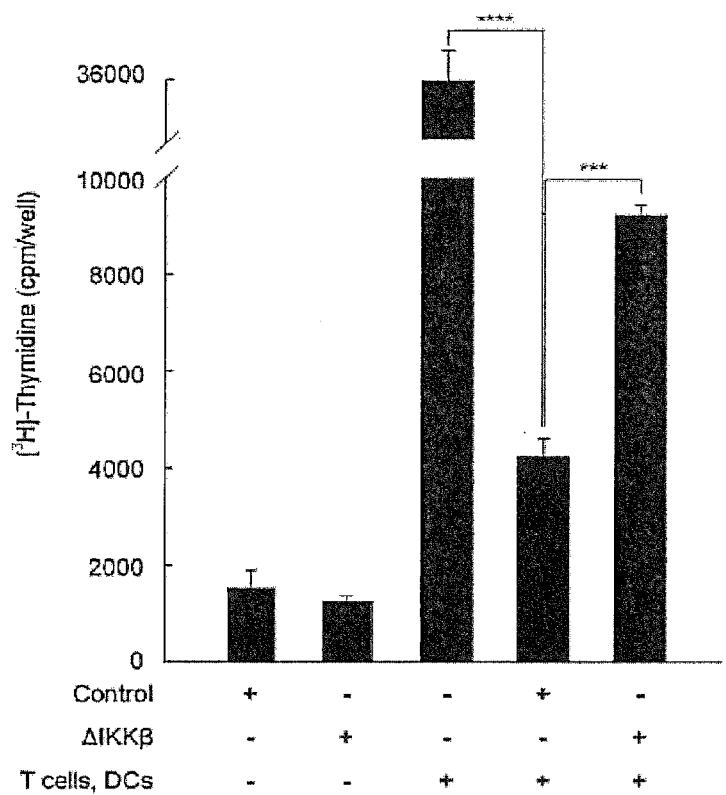

As a result, co-cultivate of fibroblasts from KO mouse with dendritic cells caused an increase in the T cell stimulation due to antigen presentation. The results are shown in FIG. 10.

Example 6

NFκB Activity of Scleroderma Patients

Figures 1, 11:
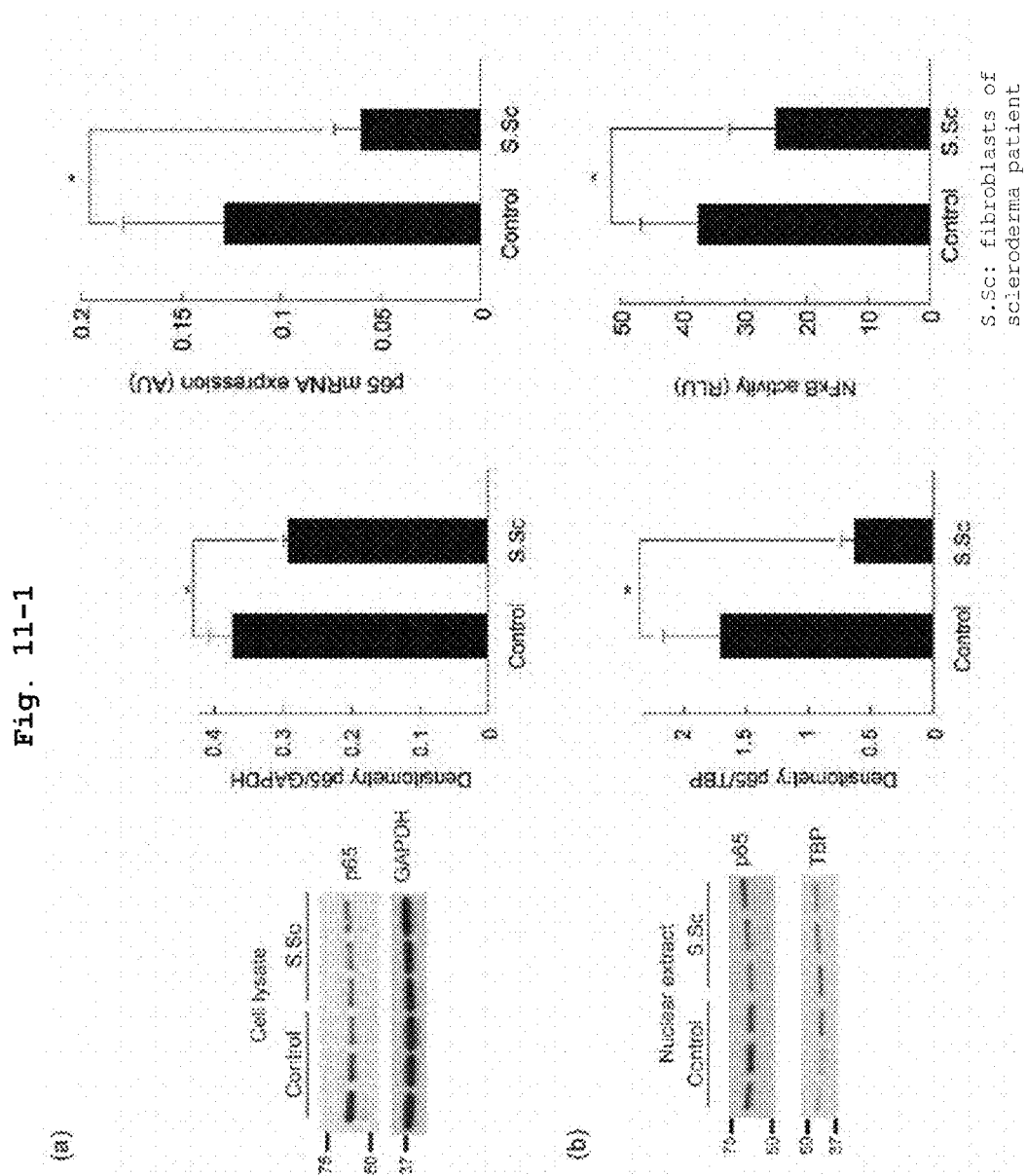
Figures 2, 11:
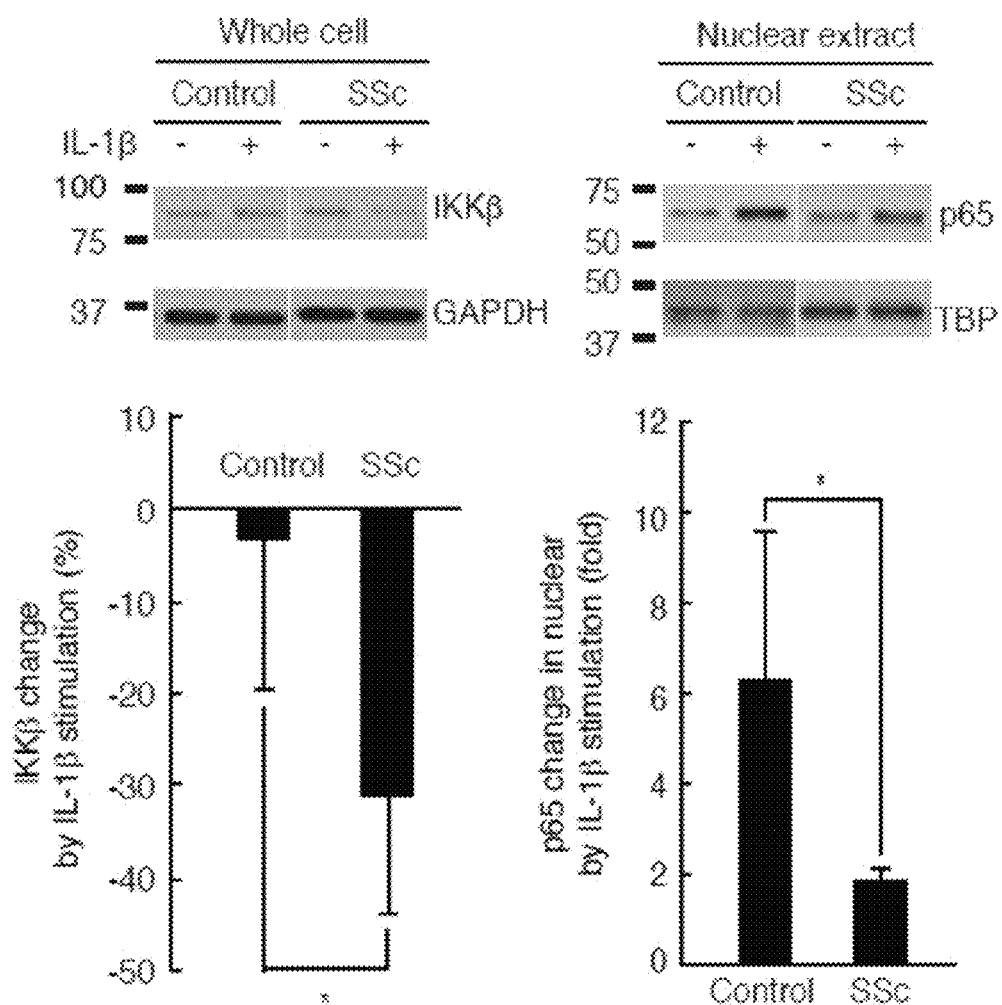
Figures 3, 11:
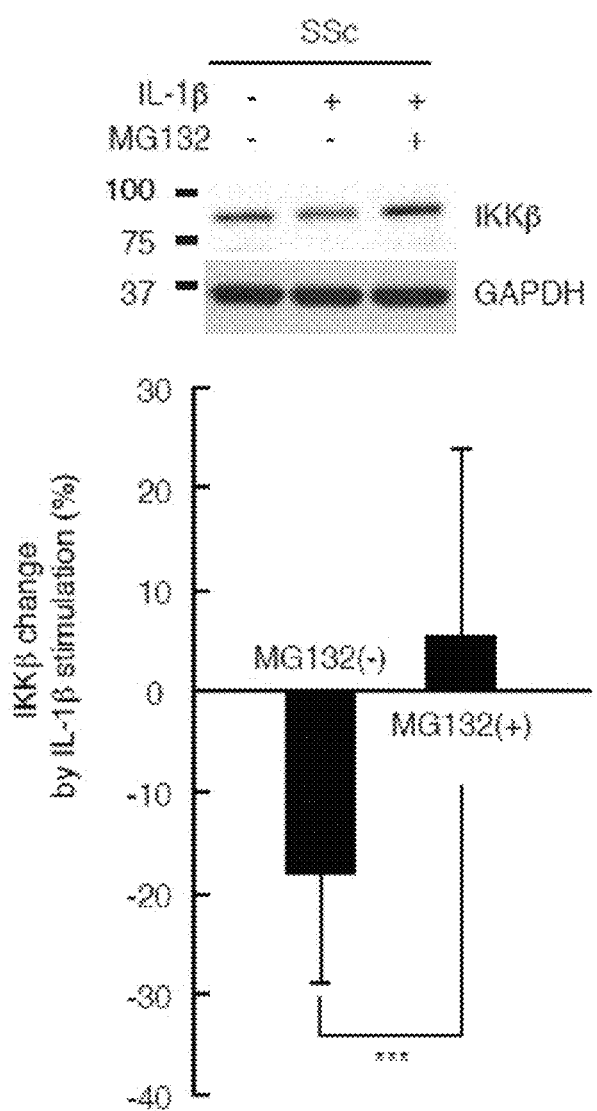

The skin of scleroderma patients (n=5) and healthy individual (n=5) was collected by biopsy, and fibroblast was prepared. The fibroblast was cultured in DMEM medium added with L-glutamine, penicillin/streptomycin and 10% FCS at 37° C., 5% $CO_2$ concentration. After culture, nuclear protein was extracted from the fibroblast by using NE-PER nuclear protein cytoplasmic protein separation extraction kit (Thermo Scientific), and the p65 protein levels of the whole-cell lysate and nuclear extract were compared. RNA was isolated from the fibroblast by using RNA aqueous (trade mark) kit (Applied Biosytems (trade mark)), and the p65 mRNA level was compared using TaqMan (registered trade mark) Gene Expression Assays kit (Applied Biosytems (trade mark)). The NFκB activity of the fibroblast was measured by NFκB p65 Transcription Assay Kit (Thermo Scientific) and compared. The expression level of NFκB p65 in the fibroblast from the skin of scleroderma patients decreased in the nucleus and whole cell (FIGS. 11-1(a), (b)), and the mRNA level also decreased (FIG. 11-1(a)). The NFκB activity also decreased (FIG. 11-1(b)). Further, fibroblasts from the skin of scleroderma patients were stimulated for 60 min with IL-1β (2.5 ng/mL), and IKKβ and nuclear p65 protein amounts were compared. As a result, the expression of IKKβ and nuclear p65 protein level was markedly suppressed by IL-β stimulation (FIG. 11-2). In addition, fibroblast from the skin of scleroderma patients was treated with 2 μM MG132 for 2 hr before the aforementioned IL-β stimulation, and the IKKβ level was measured. As a result, the MG132 treatment recovered the IKKβ level (FIG. 11-3).

That is, it was shown that a decrease in the NFκB activity and p65 expression level was caused by a decrease in the expression level of IKKβ. In addition, a decrease in the expression level of IKKβ in the fibroblast of scleroderma patients was suggested to involve degradation of ubiquitin-proteasome system.

While the present invention has been described with emphasis on preferred embodiments, it is obvious to those skilled in the art that the preferred embodiments can be modified. The contents disclosed in any publication including specifications of patent applications are hereby incorporated in their entireties by reference, to the extent that they have been disclosed herein.

INDUSTRIAL APPLICABILITY

The present invention provides a non-human animal that shows fibrosis of various tissues since it lacks IKKβ gene in a myofibroblast- and/or smooth muscle cell-specific manner. In addition, the non-human animal can be used for the elucidation of the mechanism of fibrosis, and the development of a prophylactic or therapeutic drug for fibrosis.

Since the non-human animal shows high similarity to the pathology found in human scleroderma, it can also be used as an animal model of scleroderma. Scleroderma is an intractable disease with an unknown cause, and the non-human animal is extremely useful since it can provide an "animal model" useful for the elucidation of the mechanism thereof and the development of a prophylactic or therapeutic drug therefor.

This application is based on a U.S. provisional patent application No. 61/721,301 (filing date: Nov. 1, 2012), the contents of which are incorporated in full herein.

---

---

The invention claimed is:

1. A mouse showing fibrosis in at least skin, esophagus, lungs and kidney, which lacks biallelic IKKβ genes in a myofibroblast- and/or smooth muscle cell-specific manner, or a part of the living body thereof,
    wherein a nucleic acid encoding a site-specific recombination enzyme which is linked downstream of a myofibroblast- and/or smooth muscle cell-specific promoter is inserted into the mouse genome,
    wherein the IKKβ genes in both alleles are flanked by recognition sites of the recombination enzyme, and
    wherein combination of the recombination enzyme and the recognition site is Cre-loxP or FLP-FRT.

2. The mouse or a part of the living body thereof according to claim 1, which is a scleroderma model.

3. A method of screening for a substance for the prophylaxis and/or treatment of fibrosis in skin, esophagus, lungs or kidney, comprising
    (a) a step of contacting a test substance with the mouse or a part of the living body thereof according to claim 1, and (b) a step of analyzing fibrosis in skin, esophagus, lungs or kidney of the aforementioned mouse or a part of the living body thereof according to claim 1.

4. A method of screening for a substance for the prophylaxis and/or treatment of scleroderma, comprising
   (a) a step of contacting a test substance with the mouse or a part of the living body thereof according to claim 1, and
   (b) a step of analyzing an event reflecting pathology scleroderma of the aforementioned mouse or a part of the living body thereof according to claim 1.

5. The mouse or a part of the living body thereof according to claim 1, wherein the promoter is selected from Sm22α promoter, αSMA promoter and SMMHC promoter.

6. The mouse or a part of the living body thereof according to claim 5, wherein the promoter is Sm22α promoter.

7. The mouse or a part of the living body thereof according to claim 2, wherein the promoter is selected from Sm22α promoter, αSMA promoter and SMMHC promoter.

8. The mouse or a part of the living body thereof according to claim 7, wherein the promoter is Sm22α promoter.

9. The mouse or a part of the living body thereof according to claim 1, wherein the combination of the recombination enzyme and the recognition site is Cre-loxP.

10. The mouse or a part of the living body thereof according to claim 2, wherein the combination of the recombination enzyme and the recognition site is Cre-loxP.

11. The mouse or a part of the living body thereof according to claim 5, wherein the combination of the recombination enzyme and the recognition site is Cre-loxP.

12. The mouse or a part of the living body thereof according to claim 6, wherein the combination of the recombination enzyme and the recognition site is Cre-loxP.

13. The mouse or a part of the living body thereof according to claim 7, wherein the combination of the recombination enzyme and the recognition site is Cre-loxP.

14. The mouse or a part of the living body thereof according to claim 8, wherein the combination of the recombination enzyme and the recognition site is Cre-loxP.

* * * * *